(12) United States Patent
Borca et al.

(10) Patent No.: US 7,332,170 B1
(45) Date of Patent: Feb. 19, 2008

(54) CLASSICAL SWINE FEVER VIRUS VIRULENCE DETERMINANT AND A NOVEL CLASSICAL SWINE FEVER VACCINE

(75) Inventors: Manuel V. Borca, Westbrook, CT (US); Guillermo R. Risatti, Westbrook, CT (US); Daniel L. Rock, Monticello, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/316,755

(22) Filed: Dec. 23, 2005

(51) Int. Cl.
*A61K 39/12* (2006.01)
*A61K 39/00* (2006.01)
*C12N 15/09* (2006.01)
*C12Q 1/68* (2006.01)

(52) U.S. Cl. .............................. 424/218.1; 424/185.1; 424/199.1; 424/204.1; 424/205.1; 435/6; 435/69.3

(58) Field of Classification Search .................... None
See application file for complete search history.

(56) References Cited

OTHER PUBLICATIONS

H.G.P. van Gennip et al., Experimental non-tranmissable marker vaccines for classical swine fever (CSF) by trans-complementation of E or E2 of CSFV, Vaccine, 2002, vol. 20, pp. 1544-1556.*
H.G.P. van Gennip et al., Chimeric classical swine fever viruses containing envelope protein E or E2 of bovine diarrhoea virus protect pigs against challenge with CSFV and induce a distinguishable antibody response, Vaccine, 2001, vol. 19, pp. 447-459.*
Lin et al., Identification of antigenic regions of the E protein for pig antibodies elicited during classical swine fever virus infection, Journal of Biochemistry, 2004, vol. 136, pp. 795-804.*
Lin et al., Deletions of structural glycoprotein E2 of classical swine fever virus strain Alfort/187 resolve a linear epitope of monoclonal antibody WH303 and the minimal N-terminal domain essential for binding immunoglobulin G antibodies of a pig hyperimmune serum, Journal of Virology, Dec. 2000, vol. 74, No. 24, pp. 11619-11625.*

* cited by examiner

*Primary Examiner*—Bruce R. Campell
*Assistant Examiner*—Sharon Hurt
(74) *Attorney, Agent, or Firm*—John Fado; Evelyn Rabin

(57) ABSTRACT

Transposon linker insertion mutagenesis of a full-length infectious clone of the highly pathogenic classical swine fever virus (CSFV) isolate Brescia (pBIC) was used to identify genetic determinants of CSFV virulence and host range. A virus mutant, RB-C22 (RB-C22v), possessing a 19-residue tag insertion at the carboxyl end of E1 was constructed. RB-C22v and the parental virus pBIC (pBICv) exhibited similar growth characteristics on primary porcine macrophage cell cultures although RB-C22v produced significantly smaller plaques on SK6 cell cultures. In vivo, RB-C22v was markedly attenuated in swine. In contrast with pBIC infection, where mortality was 100%, all RB-C22v-infected pigs survived infection remaining clinically normal. Additionally, chimeras of the Brescia strain and the attenuated vaccine strain CS were constructed and evaluated for viral virulence in swine. Chimeras 138.8v and 337.14v, chimeras containing the E2 glycoprotein of CS and chimeric virus 319.1v, which contained only the CS E2 glycoprotein in the Brescia background, were attenuated in swine. Chimeras encoding all Brescia structural proteins in a CS genetic background remained attenuated, indicating that additional mutations outside the structural region are important for CS vaccine virus attenuation. The combined results indicate a significant role for E1 glycoprotein and E2 glycoprotein in swine virulence.

14 Claims, 21 Drawing Sheets

Fig. 1B pBICv            RB-C22v

CLASSICAL SWINE FEVER VIRUS VIRULENCE DETERMINANT AND A NOVEL CLASSICAL SWINE FEVER VACCINE

BACKGROUND OF THE INVENTION

1. Field of the Invention

This invention relates to the isolation and characterization of novel Classical Swine Fever Virus (CSFV) virulence determinants associated with E1 glycoprotein function and E2 glycoprotein function and utilization of these novel virulence determinants to design live attenuated CSF vaccines.

2. Description of the Relevant Art

Classical swine fever (CSF) is a highly contagious and often fatal disease of swine, which is characterized by fever and hemorrhages and can present with either an acute or a chronic course (van Oirschot, J. T. 1986. In: *Diseases of Swine,* 6th edition, Leman et al., eds., Iowa State University Press, Ames, Iowa, page 289). The causative agent is classical swine fever virus (CSFV). Infection with highly virulent CSFV strains generally leads to death in infected animals, whereas isolates of moderate to low virulence induce a prolonged chronic disease. The genetic basis of CSFV virulence and host range is poorly understood (van Oirschot, supra).

CSFV is enzootic in all continents, and actively circulating in South and Central America, southern Mexico, and the Caribbean. Disease outbreaks occur intermittently in Europe where control programs of the disease (Westergaard et al., 1998. In: *Vaccines in Agriculture: Immunological Applications To Animal Health and Production*, Wood et al., eds., CSIRO, East Melbourne, Australia, pages 13-20) include quarantine and eradication of infected herds, resulting in the elimination of a large number of animals, including noninfected animals, thus engendering significant economic losses. Vaccination, quarantine and testing protocols offer an alternative to these measures and may become the only means to control and eradicate an outbreak of CSF, reducing the economic impact that results from the heretofore elimination of such a vast number of pigs.

Safe and effective CSFV vaccines that prevent clinical symptoms of the disease and virus spreading, including during the early post-vaccination period, have been used around the world (Aynaud, J. M. 1988. In: *Classical Swine Fever and Related Viral Infections*, B. Liess, ed., Nijhoff, Boston, Mass., pages 165-176; Biront and Leunen. 1988. ibid., pages 181-197). Among available CSFV vaccines, live attenuated vaccines, such as C strain, GPE-strain, Thiversal strain, and PAV-250, confer effective and long lasting immunity against CSF (Biront and Leunen, ibid.). In general, these vaccines have been obtained after serial passages of CSFV isolates in tissue culture or rabbits; however, the genetic bases of the attenuation in the above cases are unknown. Additionally, it is not currently possible to distinguish, serologically, between animals vaccinated with live attenuated vaccines and animals infected with wild-type virus.

Development of infectious CSFV cDNA clones has enabled genetic approaches for defining mechanisms of viral replication and pathogenesis. Infectious clones of the attenuated CSFV C-strain and the pathogenic Alfort/Tübingen strain have been constructed, enabling identification of $E^{ms}$ and $N^{pro}$ as virulence factors in swine and the role of different $E^{ms}$ mutations in virus attenuation (Meyers et al. 1996, supra, Moormann et al. 1996. *J. Virol.* 70: 763-770, Ruggli et al. 1996. *J. Virol.* 70:3478-3487, Mayer et al. 2004. *Vaccine* 22: 317-328). CSFV infectious clones have been used to identify viral proteins or protein domains functioning in viral replication and virulence, and to engineer attenuated marker CSF live attenuated vaccines (Meyers et al. 1999, supra, Moser et al. 2001. *Virus Genes* 23: 63-68, Tratschin et al. 1998. *J. Virol.* 72: 7681-7684, van Gennip et al., supra).

CSFV is a member of the Pestivirus genus of the Flaviviridae family (Francki et al. 1991. *Archives of Virol. Suppl.* 2:223). CSFV is a small enveloped virus with a single-stranded, 12.5 kb RNA genome of positive polarity which contains a long open reading frame encoding a 3000 amino acid polyprotein with a gene order: $NH_2$-Npro-C-$E^{ms}$-E1-E2-p7-NS2-NS3-NS4A-NS4B-NS5A-NS5B-COOH. The polyprotein gives rise to 11 to 12 final cleavage products by co- and posttranslational processing involving cellular and viral proteases (Rice, C. M. 1996. In: *Fundamental Virology*, Third edition, Fields et al., eds., Lippincott Raven, Philadelphia, Pa., pages 931-959). Protein C and the glycoproteins $E^{ms}$, E1 and E2 represent structural components of the virion (Thiel et al. 1991. *J. Virol.* 65: 4705-4712). E1 and E2 are anchored to the envelope by their carboxy termini, with $E^{ms}$ loosely associated with the envelope. $E^{ms}$ and E2 are present as homodimers linked by disulfide bridges on the surface of CSFV virions; E2 is also found dimerized with E1 (Weiland et al. 1990. *J. Virol.* 64: 3563-3569; Weiland et al. 1999. *J. Gen. Virol.* 80 (Pt 5): 1157-1165). Although $E^{ms}$ and E2 have been shown to function in viral pathogenesis and the induction of a protective immune response, respectively (Hulst et al. 1997. *J. Gen Virol.* 78 (Pt 11): 2779-2787; Hulst et al. 1998. *J. Virol.* 72: 151-157; Meyers et al. 1999. *J. Virol.* 73: 10224-10235; Meyers et al. 1996. *J. Virol.* 70: 1588-1595; van Gennip et al. 2000. *Vaccine* 19: 447-459; Weiland et al. 1990, supra), the function of E1 remains unknown. The genetic basis of CSFV virulence and host range remains poorly understood (van Oirschot, supra).

Candidate CSFV subunit marker vaccines have been developed using recombinant E2 envelope protein (Van Zijl et al. 1991. *Vaccine* 17: 433-440; Hooft van Iddkinge et al. 1996. *Vaccine* 14: 6-12; Hulst et al. 1993. *J. Virol.* 67: 5435-5442; Van Rijn et al. 1996. *J. Gen. Virol.* 77: 2737-2745; Van Rijn et al. 1998. *Vaccine* 17: 433-440). E2, the major structural protein, induces neutralizing antibodies and protective immunity in infected and vaccinated pigs (Wensvoort et al. 1989. *Vet. Microbiol.* 21: 9-20; Van Zijl et al., supra; Hulst et al., 1993, supra; Rumenapf et al. 1991. *J. Virol.* 65: 589-597; Van Rijn et al., supra). Different E2 protein domains have been described as targets for neutralizing monoclonal antibodies (Wensvoort et al., supra), but E2 subunit vaccines have not been found to be as efficacious as traditional live attenuated vaccines, particularly when animals are challenged shortly after vaccination (Hulst et al., 1993, supra; Van Rijn et al., supra; Risatti et al. 2003. *J. Clin. Microbiol.* 41: 500-505). The failure to induce rapid and efficient protective immunity precludes the use of subunit vaccines as an emergency control measure during a CSFV outbreak. DNA vaccines encoding E2, when expressed, also induced protection in pigs; however, again, rapid elicitation of protection was not proven (Andrew et al. 2000. *Vaccine* 17: 1932-1938; Yu et al. 2001. *Vaccine* 19: 1520-1525).

$E^{ms}$ has been shown to function in viral virulence (Meyers et al. 1999, supra). Depending on the extent of the engineered mutation, specific Alfort/187 $E^{ms}$ mutants exhibited different degrees of attenuation when inoculated in swine, indicating a role for $E^{ms}$ in viral pathogenesis (Meyers et al. 1999, supra). Additionally, attempts to mutate and inactivate $E^{rns}$ in the attenuated C-strain resulted in a virus atypically cytopathic for cell cultures (Hulst et al. 1998, supra, Widjojoatmodjo et al. 2000. *J. Virol.* 74: 2973-2980).

CSF infectious clones have also been used to examine the function of other viral proteins and genomic regions. The $N^{pro}$ gene of the Alfort/187 strain was replaced with the ubiquitin gene as a marker. In vitro replication kinetics of the recombinant and parental strains were indistinguishable, indicating that $N^{pro}$ is non-essential for virus growth in vitro (Tratschin et al., supra). Similarly, insertion of 44 bases within the 5' non-translated region of the Alfort/187 genome also failed to affect in vitro replication kinetics (Moser et al., supra). Thus, CSFV infectious clones hold great promise for identifying viral proteins or protein domains functioning in viral virulence and host range.

Several live vector vaccines have been developed, using vaccinia, pseudorabies and adenoviruses (Van Zijl et al., supra; Rumenapf et al., supra; Konig et al. 1995. *J. Virol.* 69: 6479-6486; Peeters et al. 1997. *J. Gen. Virol.* 78: 3311-3331; Hammond et al. 2000. *Vaccine* 18: 1040-1050); however, limited potency, the possibility of antibodies specific for the vectors, and the unwanted introduction of recombinant vaccinia or adenovirus into the swine population have discouraged the use of this approach for controlling CSFV.

Recently, infectious clone technology has enabled antigenic modification of attenuated CSFV strains for use as experimental marker live attenuated CSF vaccines. Infectious clones of the attenuated C-strain were used to replace the antigenic region of E2 and/or the complete $E^{rns}$ gene with analogous sequences from Bovine Viral Diarrhea Virus (BVDV). Preliminary data indicated that both chimeric viruses were able to induce protection in pigs at one week after vaccination. Significantly, chimera-induced anti-CSFV antibody responses could be discriminated from those produced by parental virus (van Gennip et al., supra; Risatti et al., supra). Additionally, this approach, based on the replacement of homologous regions of the antigenically related Pestivirus (BVDV) in the genome of the attenuated vaccine C-strain, precludes the introduction of positive/negative markers in specific areas of the genome due to the lack of knowledge of the virulence host range determinant in CSFV. Recently, encouraging results have been obtained with a C-strain $E^{rns}$ deletion mutant complemented in trans with an $E^{rns}$ expressing cell line, resulting in a non-replicative live attenuated vaccine (Widjojoatmodjo et al., supra). Further experiments will be conducted to validate elicitation of rapid protection, as is provided by the replicative parental C-strain.

Thus, knowing the determinants of virulence would allow the introduction of precise modification at particular sites of the genome that will result in the attenuation of the virus. If antigenic markers are genetically engineered at those sites, such attenuate viruses can be applied as marker vaccines to the control of a CSF outbreak, allowing the identification and eradication of infected animals/herds, thereby preventing the elimination of uninfected animals.

SUMMARY OF THE INVENTION

We have identified novel CSFV virulence determinants; one virulence determinant is associated with E1 glycoprotein function, another is associated with E2 glycoprotein function.

In accordance with this discovery, it is an object of the invention to provide a recombinant classical swine fever virus (CSFV) comprising DNA encoding a modified CSFV E1 glycoprotein or a modified CSFV E2 glycoprotein.

It is also an object of the invention to provide a recombinant classical swine fever virus comprising DNA which has been modified to encode an CSFV E1 glycoprotein comprising a 19 mer peptide insertion.

It is a further object of the invention to provide a recombinant classical swine fever virus comprising DNA encoding CSFV E2 glycoprotein which has modified by replacing the E2 gene of the highly pathogenic strain Brescia with the E2 gene from vaccine strain CS, a modification resulting in attenuation of CSFV.

An additional object of the invention is to provide a rationally designed live attenuated CSF vaccine.

Another object of the invention relates to a method of producing a recombinant classical swine fever virus comprising DNA encoding a modified CSFV E1 glycoprotein or a modified CSFV E2 glycoprotein.

An added object of the invention is to provide immunogenic compositions comprising a viable recombinant classical swine fever virus comprising a modified CSFV E1 glycoprotein or a modified CSFV E2 glycoprotein.

Also part of this invention is a kit, comprising an immunogenic composition for generating an immune response against classical swine fever virus.

Other objects and advantages of this invention will become readily apparent from the ensuing description.

BRIEF DESCRIPTION OF THE DRAWINGS

FIG. 1B represents the growth curve of CSFV Brescia (open circles) and CS (open squares) and viruses derived from the infectious clones BIC (filled circles) and CSIC (filled squares). Primary macrophage cell cultures were infected at a MOI of 0.1 and harvested at the indicated time points. Harvested samples were titrated in SK6 cells and the presence of virus detected by immunohistochemistry as described in the examples. Data are means and standard errors from three independent experiments.

TCID$_{50}$ of CSFV pBICv or RB-C22v, overlaid with 0.5% agarose, and incubated at 37° C. for 3 days. They were then fixed with 50% (v/v) ethanol/acetone and stained by immunohistochemistry as described in the examples.

Figure 5:
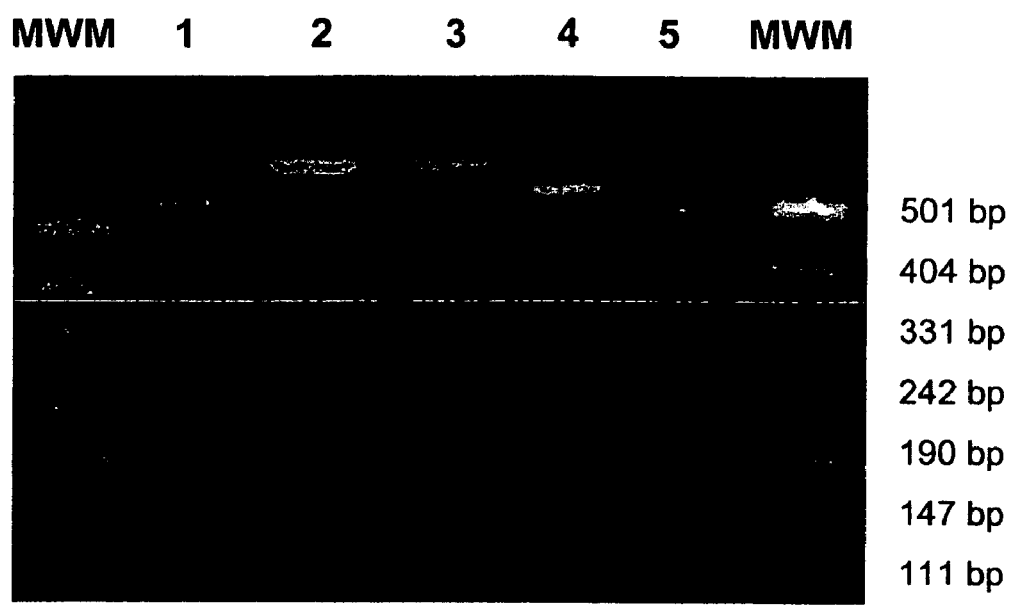

FIG. 5 depicts the identification of RB-C22 and Brescia viruses by RT-PCR in tonsils of vaccinated/challenged pigs. Lane description: (Lane 1) Pig challenged with Brescia after 1 day of being infected with RB-C22v, upper band corresponds to RB-C22v, while lower band corresponds to Brescia; (Lane 2) Pig with Brescia after 3 days of being infected with RB-C22v, only RB-C22v is detected. RB-C22 (Lane 3) and Brescia (Lane 4) stock viruses were used as control. MWM: molecular weight marker shown as base pairs.

Figure 6:
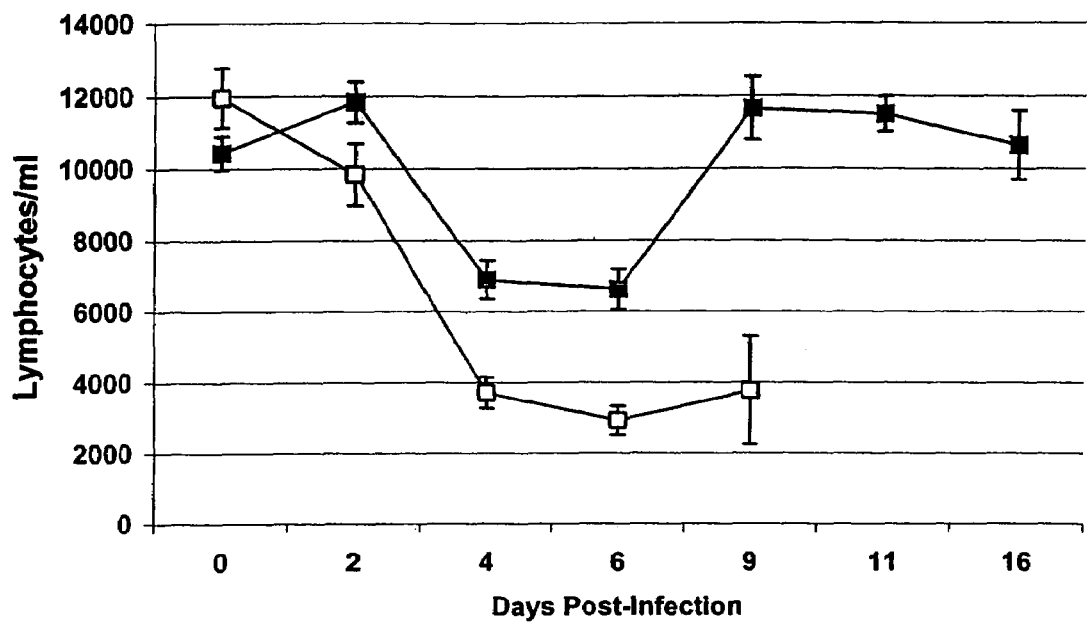
Figure 6:
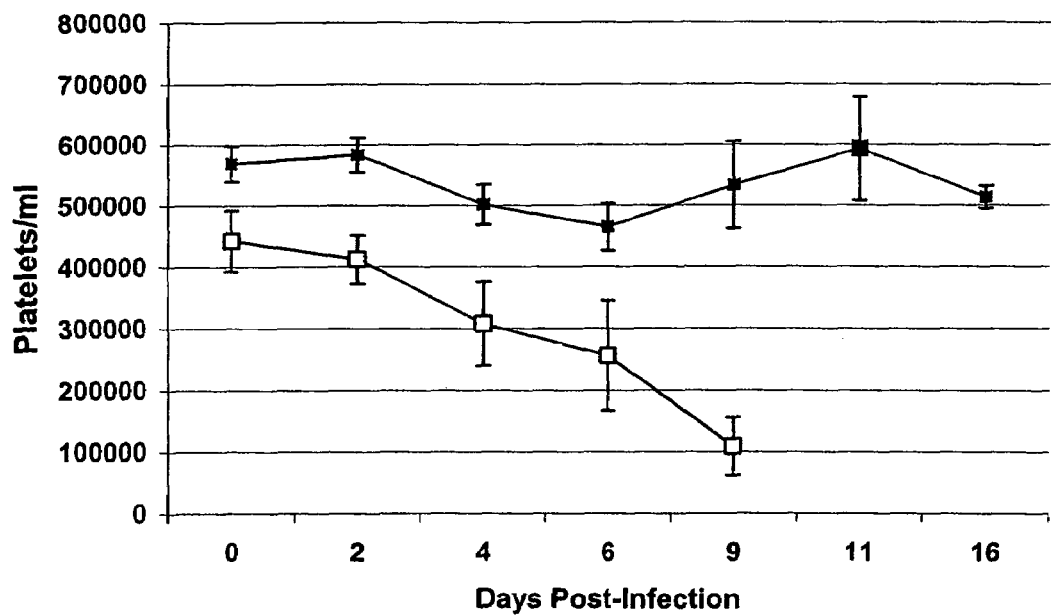

FIGS. 6A and 6B show cell counts of peripheral blood lymphocytes (FIG. 6A) and platelets (FIG. 6B) in pigs infected with pBICv (open squares) or RB-C22v (filled squares). Counts were determined as described in the examples. Each point represents the mean and standard error of at least 3 animals or more.

Figure 7:
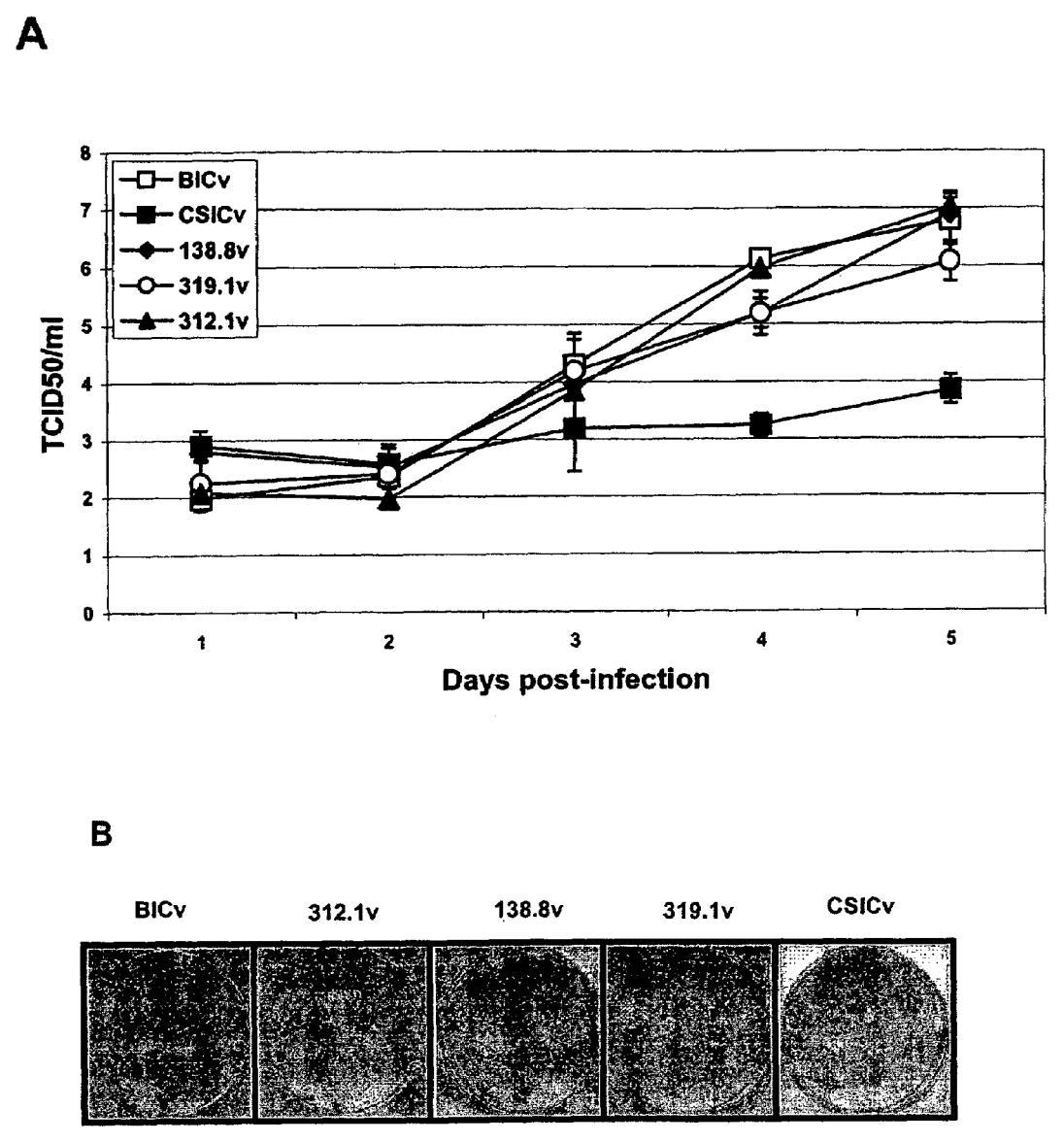

FIG. 7A depicts the growth characteristics of CSFV BICv, CSICv and chimeric viruses 138.8v, 312.1v, and 319.1v in swine macrophage cell cultures. Primary swine macrophage cell cultures were infected (MOI=0.1) with CSFV BICv (open squares), CSICv (filled squares), 138.8v (filled diamonds), 319.1v (open circles) or 312.1v (filled triangles). At times post infection, samples were collected and titrated for virus yield. Data are means and standard errors of three independent experiments. FIG. 7B depicts shows formation of CSFV BICv, CSICv and chimeric viruses on SK6 cell cultures. Cell cultures were infected with 50-100 TCID$_{50}$, overlaid with 0.5% agarose, and incubated at 37° C. for 3 days. Plates were fixed with 50% (v/v) ethanol/acetone and stained by immunohistochemistry as described in Example 7.

Figure 8A:
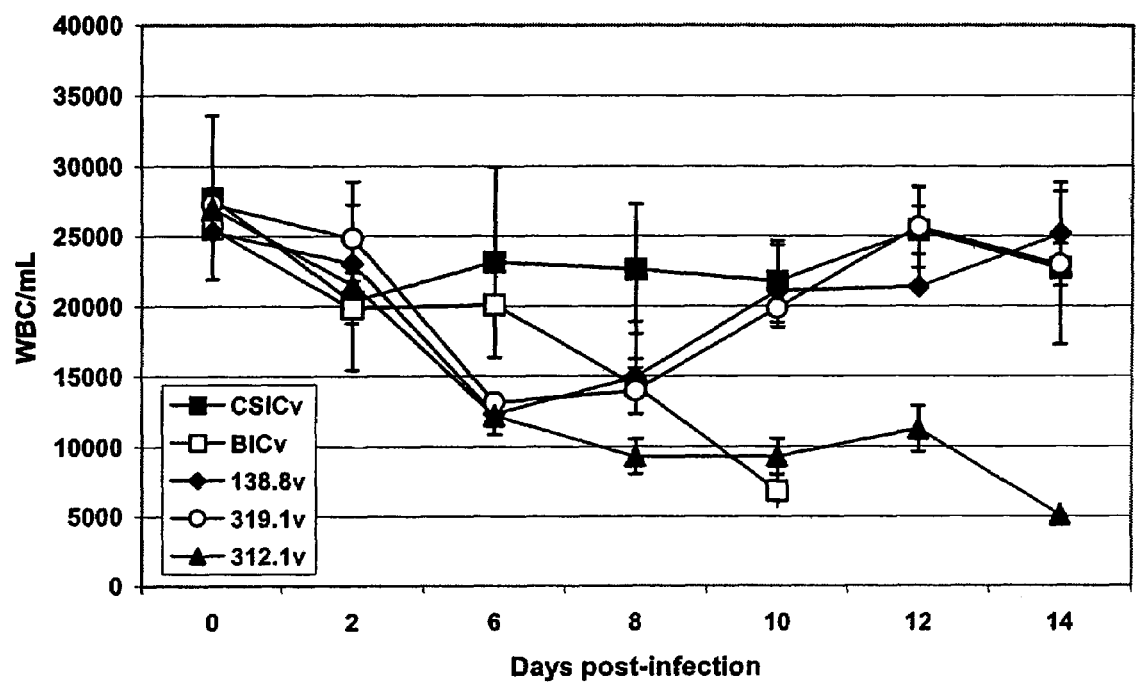
Figure 8B:
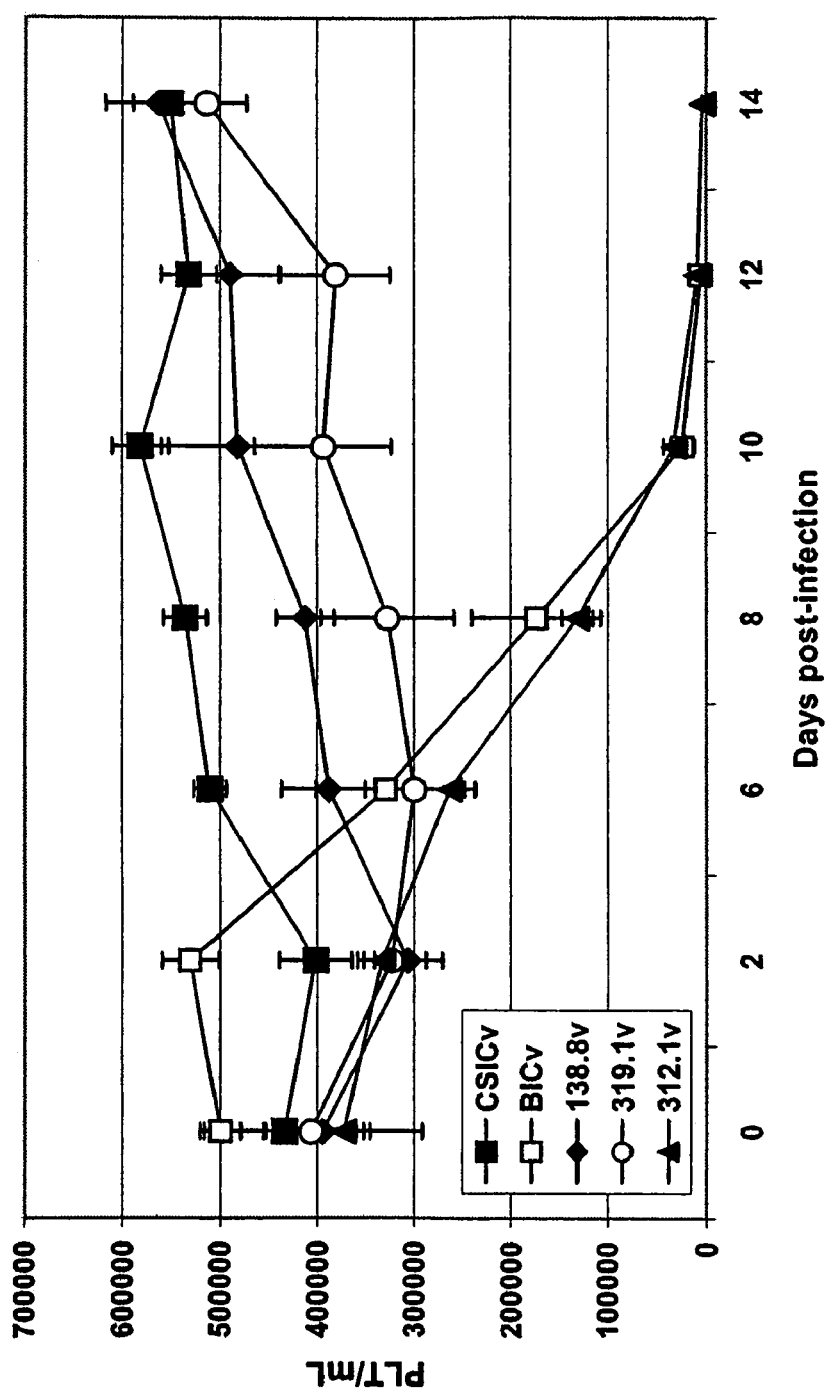

FIGS. 8A and 8B show cell counts of peripheral blood lymphocytes (FIG. 8A) and platelets (FIG. 8B) in pigs infected with BICv (open squares), CSICv (filled squares) or chimeric viruses 319.1v (open circles), 138.8v (filled diamonds), or 312.1v (filled triangles). Counts were determined as described in the examples. Each point represents the mean and standard errors of 4 or more animals.

Figure 9:
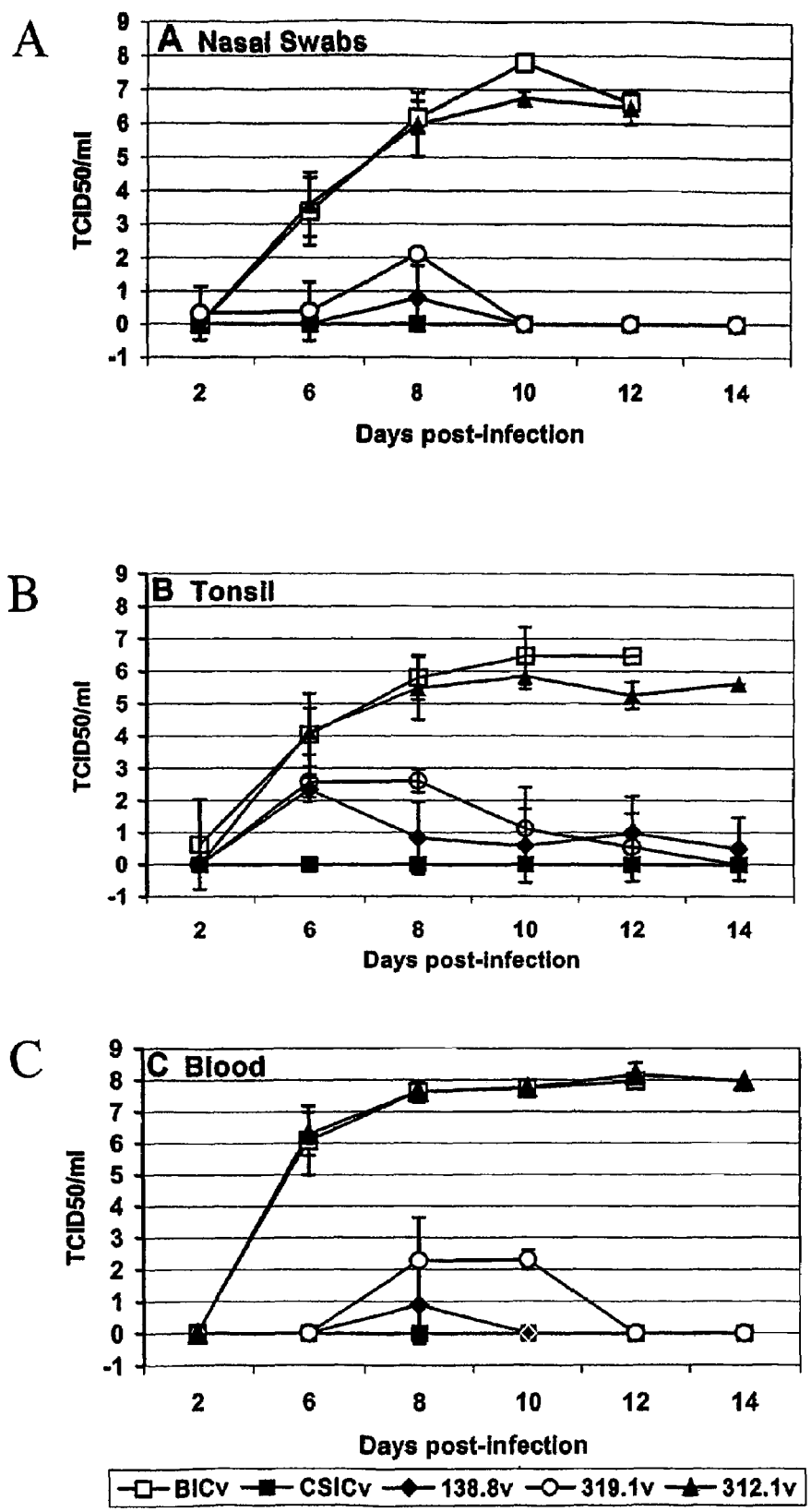

FIGS. 9A-9C depict virus titers of nasal swabs (FIG. 9A), tonsil scrapings (FIG. 9B, and blood (FIG. 9C) from pigs infected with BICv (open squares), CSICv (filled squares) or chimeric viruses 319.1v (open circles), 138.8v (filled diamonds), or 312.1v (filled triangles). Each point represents the mean and standard errors of 4 or more animals.

Figure 10:
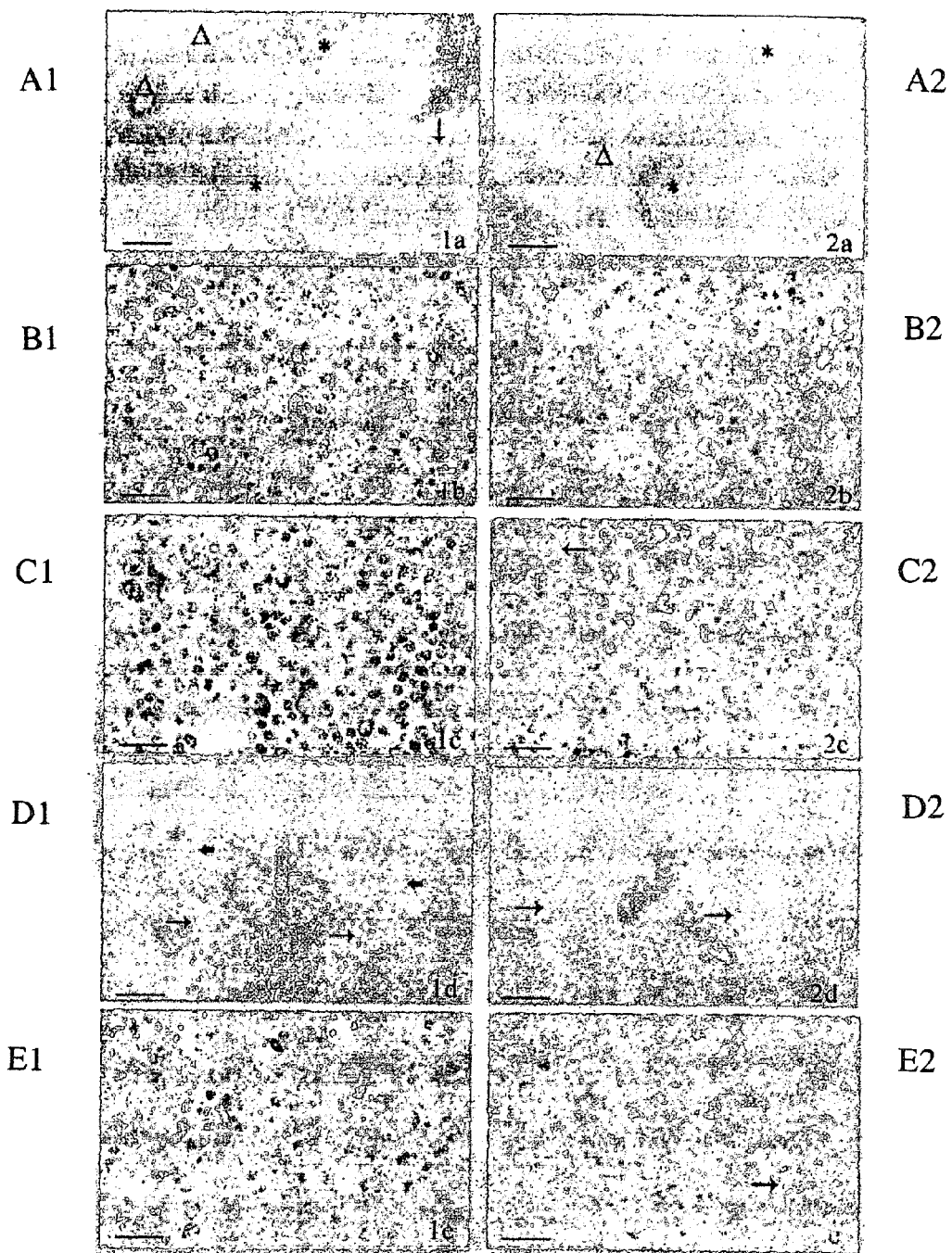

FIG. 10 depicts the detection of CSFV antigens by immunohistochemistry, at 6 days PI, in lymphoid organs of pigs infected with BICv or 319.1v. FIG. 10A1 shows the abundance of CSFV antigen I tonsillar crypt epithelium (Δ=crypt), lymphoid follicles (*), and parafollicular regions (arrow) of the BICv-infected animal. Immunoreactive cells are morphologically characterized as dendritic cells both in the follicular (FIG. 10B1) and parafollicular (FIG. 10C1) regions. In the 319.1v-infected animal (FIG. 10A2), there is minimal CSFV antigen in tonsillar crypt epithelium (Δ=crypt), and rare CSFV antigen in lymphoid follicles (*) and (FIG. 10B2) and parafollicular (FIG. 10C2) region. The spleen of the BICv-infected animal is depicted in FIG. 10D1 and shows lymphoid depletion with poorly defined periarteriolar lymphoid sheaths (large arrows) and abundant CSFV antigen in periarteriolar regions (small arrow); follicles with associated lymphoid depletion are shown in FIG. 10E1. In the 319.1v-infected animal, there are prominent periarteriolar lymphoid sheaths (FIGS. 10D2 and 10E2: arrows) with follicles, with a minimal to no expression of CSFV antigen I periarteriolar regions and follicles. Lymphoid follicles are well populated with lymphoid proliferation (FIG. 10E2). Bar in FIGS. 10A1, 10A2, 10D1, and 10D2=160 μm; in FIGS. 10B1, 10C1, 10B2, 10C2, 10E1, and 10E2=30 μm.

Figure 11:
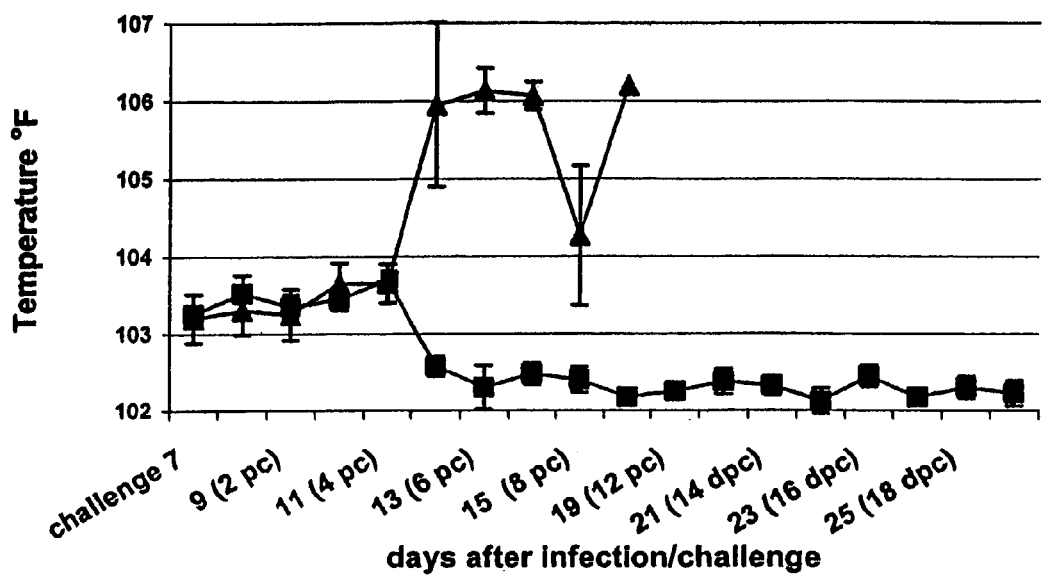
Figure 11:
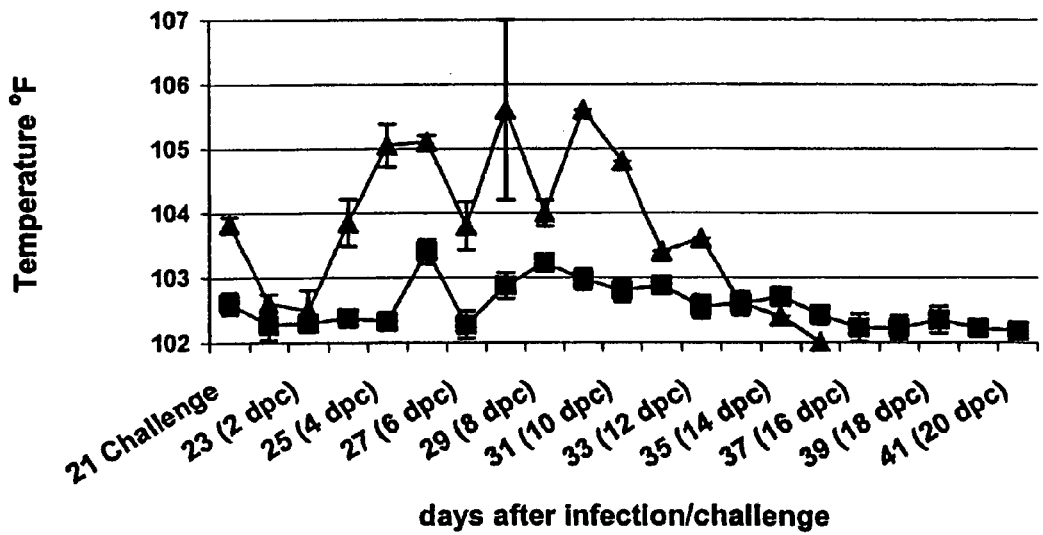

FIGS. 11A and 11B depict the body temperature curves of animals infected with RB-C22v and challenged, at 7 (FIG. 11A) or 21 (FIG. 11B) days later with Brescia virus. Each point represents the mean of animals (±SE). Curves represent values from RB-22v pre-infected (squares; n=8) and non RB-C22 pre-infected control (triangles; n=4) animals.

Figure 12A:
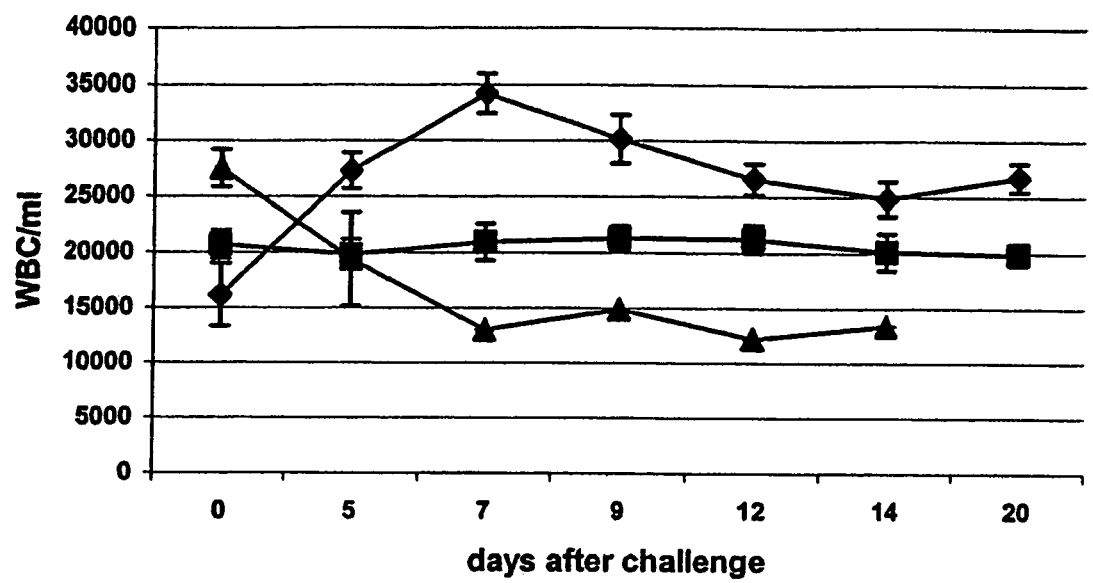
Figure 12B:
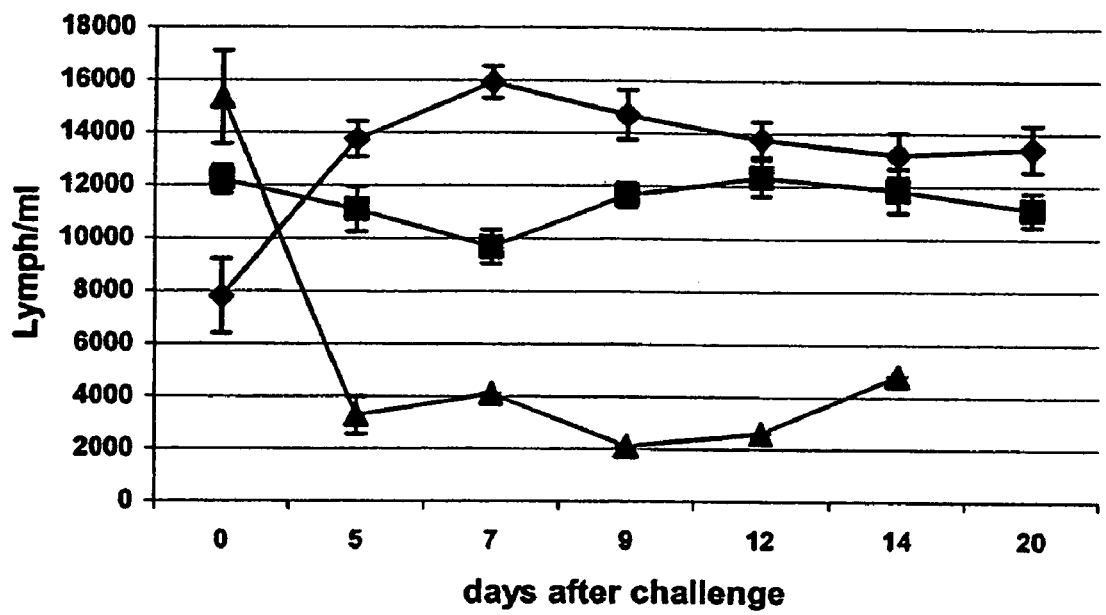
Figure 12C:
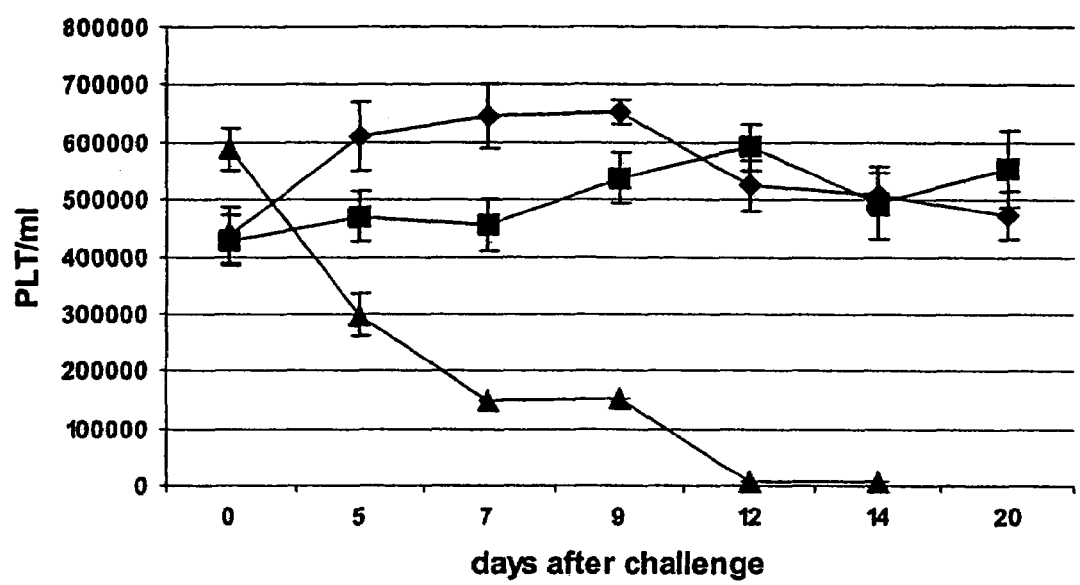

FIGS. 12A-12C show white blood cell (FIG. 12A), lymphocyte (FIG. 12B), and platelet (FIG. 12C) counts in peripheral blood of animals infected with RB-C22v and challenged, at 7 days (diamonds; n=8) or 21 days (squares; n=8) later with Brescia virus as well as non-RB-C22v-pre-infected control animals (triangles; n=4). Values are expressed as number of cells/ml and are the mean of all individuals the group (±SE).

Figure 13:
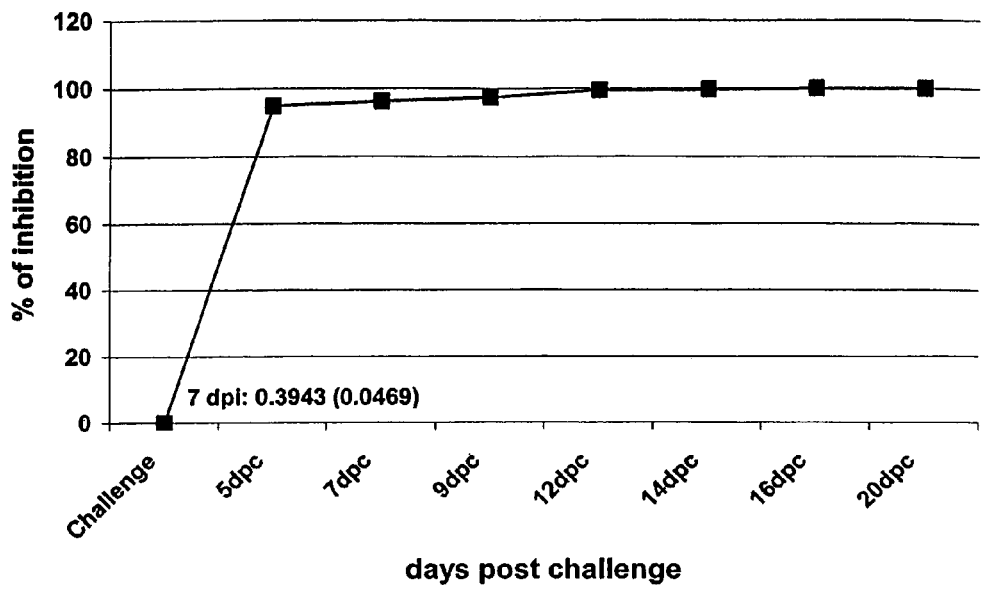
Figure 13:
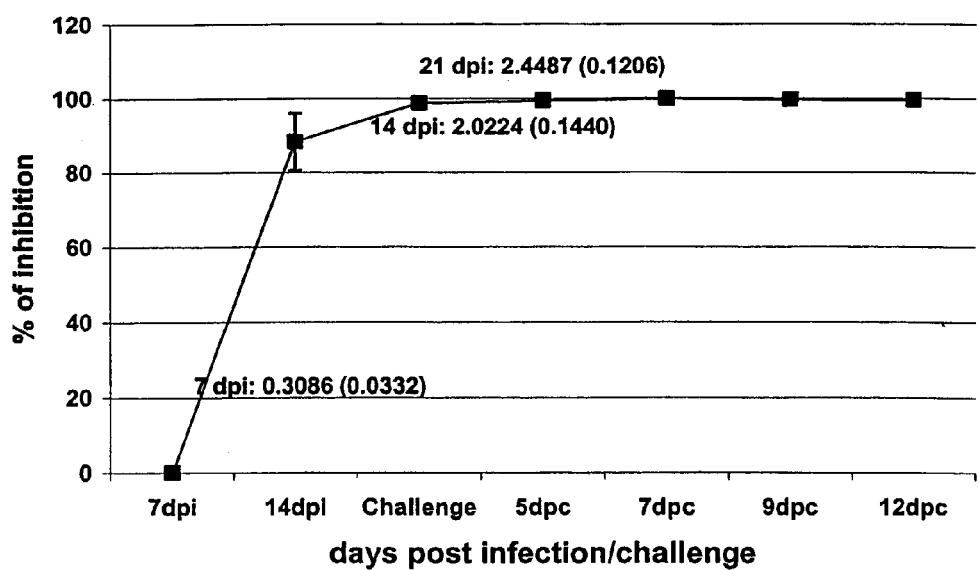

FIGS. 13A and 13B depict anti-CSFV antibody titers detected by ID DLO ELISA in sera from animals infected with RB-C22v and challenged at 7 days (FIG. 13A) or 21 days (FIG. 13B) later with Brescia virus. Values are expressed as percentage of inhibition. Each point represents the mean of 8 animals (±SE) in each group. Neutralizing antibody titers, expressed as the log 10 of the maximum serum dilution that neutralize 50% of 100 TCID$_{50}$ of pBIC, are presented at indicated days post-RB-C22v infection (±SE). Values from non-RB-C22v-pre-infected control animals (n=8) were negative by both techniques.

Figure 14A:
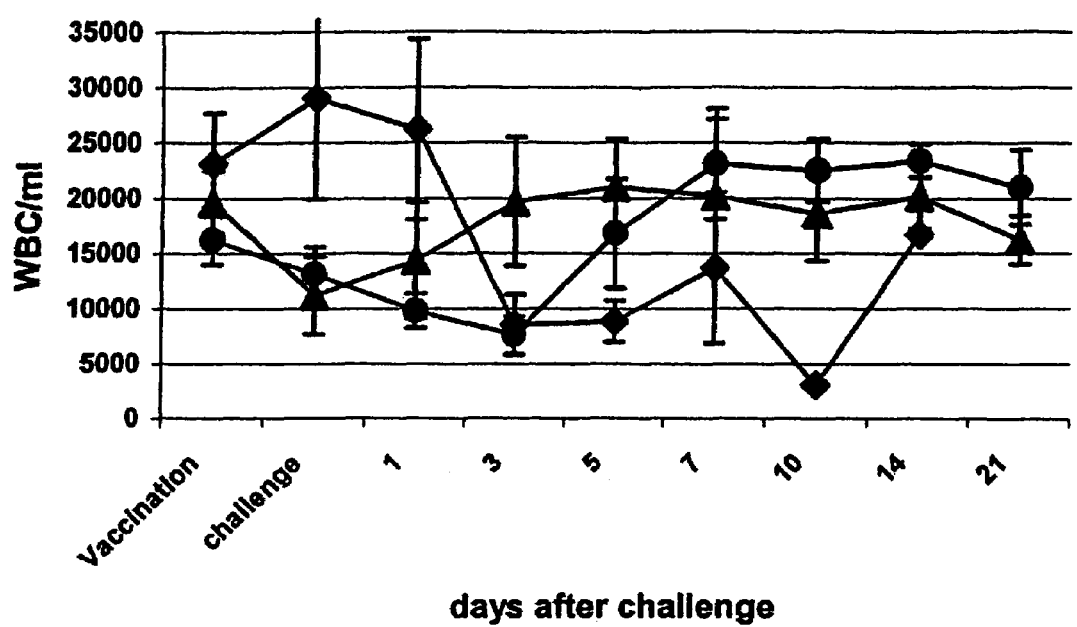
Figure 14B:
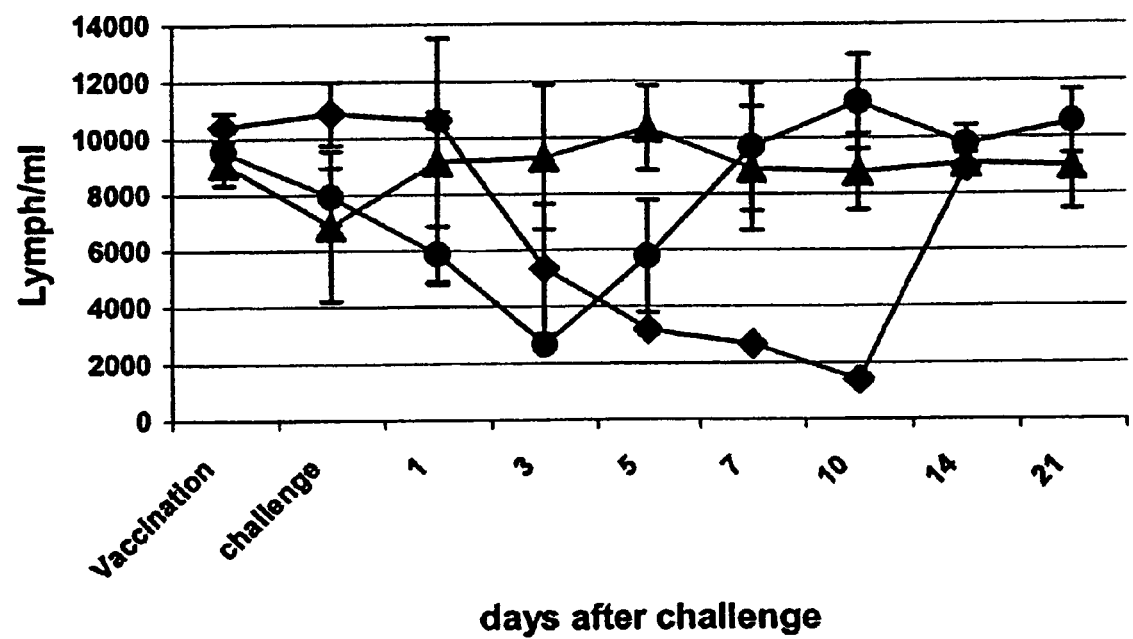
Figure 14C:
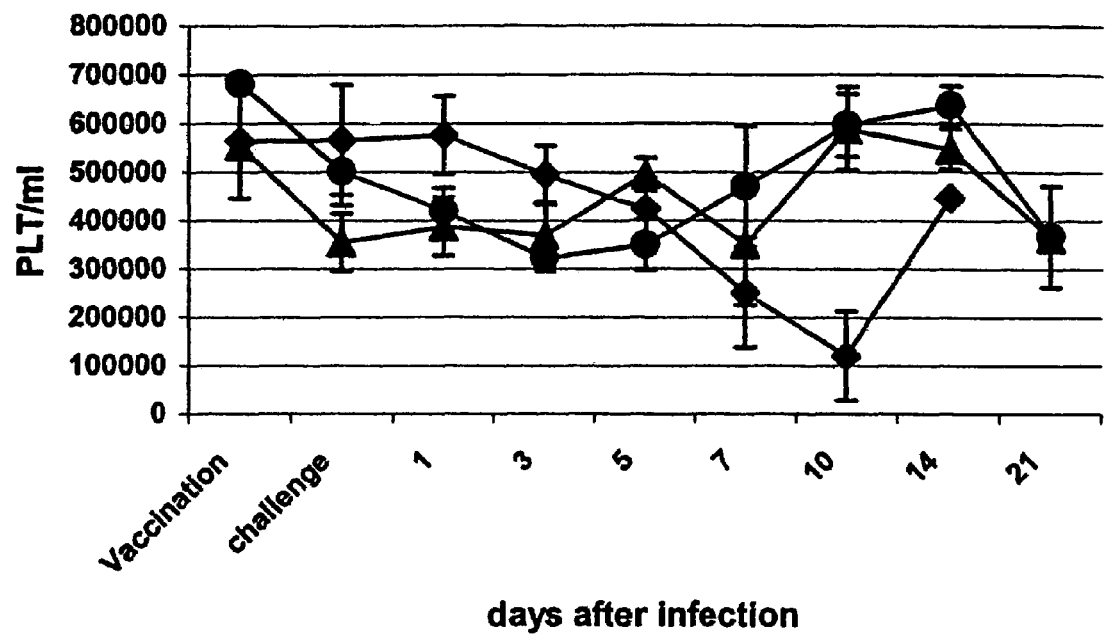

FIGS. 14A-14C show white blood cell (FIG. 14A), lymphocyte (FIG. 14B), and platelet (FIG. 14C) counts in peripheral blood of animals infected with RB-C22v and challenged at 1 day (diamonds; n=3), 3 days (circles; n=3), and 5 days (triangles; n=3) later with Brescia virus. Values are expressed as the number of cells/ml and are the mean of all individuals in the group (±SE).

DETAILED DESCRIPTION OF THE INVENTION

The development of disease control strategies in the event of a CSFV outbreak requires rapid onset of protection, which becomes a more important parameter of vaccine performance than, for example, duration of protection. The development of such vaccines would imply the production of rationally designed live attenuated vaccine CSFV strains.

The genetic basis and the molecular mechanisms underlying Pestivirus virulence remain largely unknown. In the specific case of CSFV, there are two reports implicating a specific viral protein or genomic region with virulence. A single or double codon mutation abrogating E$^{ms}$ RNAse activity of the CSFV Alfort/Tübingen strain attenuated the virus for pigs (Meyers et al. 1999, supra). Notably, a similar result was obtained by mutating the same domain of the E$^{ms}$ of BVDV (Meyer et al. 2002. J. Virol. 76: 8494-8503). More recently, N$^{pro}$ has also been shown to be involved in CSFV virulence, since deletion of Npro in the virulent Eystrup strain abrogated its virulence for swine (Mayer et al. 2004. Vaccine 22: 317-328). Here, two novel CSFV virulence determinants associated with the E1 glycoprotein and the E2 glycoprotein are described; these data indicate that a domain of glycoprotein E1 and a domain of glycoprotein E2 affect swine virulence. Although E2 has been characterized as the most immunogenic of the CSFV glycoproteins (Weiland et al. 1990., supra), thus inducing protective immune responses in swine, (Hulst et al. 1993, supra; van Zijl et al., supra;

Koning et al. 1995. *J. Virol.* 69: 6479-6486), its role in virus virulence has not been previously described.

Figure 4A:
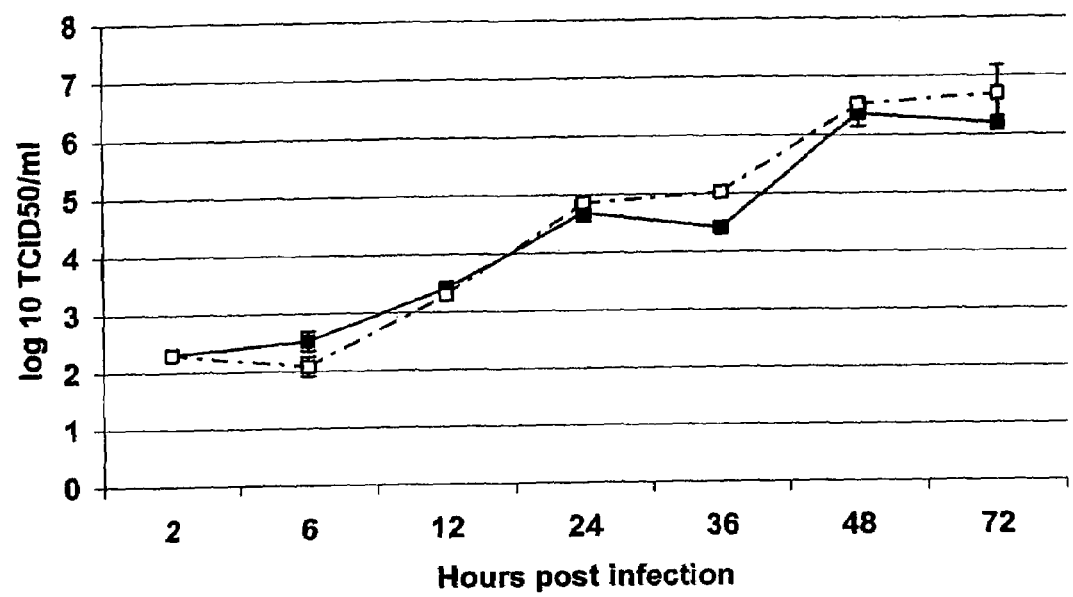
FIG. 4A shows the growth characteristics of CSFV pBICv and RB-C22v on swine macrophage cell cultures. Primary swine macrophage cell cultures were infected at an MOI of 0.1 with CSFV pBICV (open squares) or RB-C22 (filled squares). At times post infection, samples were collected and titrated for virus yield. Data are means and standard errors of three independent experiments.

To identify CSFV virulence and host range determinants, we mutated a cDNA infectious clone of the pathogenic Brescia strain using transposon linker insertion mutagenesis (TLIM) (Hallet et al. 1997. *Nucleic Acids Res.* 25: 1866-1867; Hobom et al. 2000. *J. Virol.* 74: 7720-7729). A viral mutant, RB-C22v, with a 19 amino acid insertion at nucleotide position 2429, near the carboxyl terminus of E1 glycoprotein, was obtained. Insertion of the 19 amino acid peptide results in complete in vivo attenuation of the virulent CSFV strain Brescia, rendering a virus that resembles CSFV live attenuated vaccines in infected pigs. Unlike the acute fatal disease induced by Brescia and its infectious clone pBICv, RB-C22v infection was subclinical, characterized by decreased viral replication in tonsils, limited generalization of infection, a significant reduction of virus shedding, and significantly lower virus titers in blood, lymph nodes, bone marrow, kidney, spleen, and brain. Notably, the attenuation observed for RB-C22v was independent of its ability to replicate in cell culture; RB-C22v and pBICv exhibited comparable growth characteristics in primary macrophage cell cultures (FIG. 4A).

While the exact mechanism mediating RB-C22 attenuation in pigs is unknown, it conceivably could involve some aspect of virus attachment and/or entry into critical target cells. $E^{ms}$, E1 and E2 are structural glycoproteins in the CSFV virion envelope (Weiland et al. 1990; Weiland et al. 1999; supra). Anchored to the envelope, E1 and E2, appear as both homo and heterodimers linked by disulfide bridges (Thiel et al.; Weiland et al. 1990; Weiland et al. 1999; supra). While E1 function is unknown, $E^{ms}$ and E2 are known to be involved in virus reception (Hulst et al. 1997, supra). The predicted E1 composition and structure were analyzed using Genetics Computer Group version 7 with the predict multi program and version 10 software packages (Devereuxz et al. 1984. *Nucleic Acids Res.* 12: 387-395). The analysis predicts that the 19 amino acid insertion at the carboxyl terminus of E1 in RB-C22v alters its secondary structure introducing an alpha helix and a turn close to the cleavage site between glycoproteins E1 and E2. Altered E1 protein structure may directly impact a specific, and as yet unknown, E1 virulence function or alternatively it may affect E1 ability to interact with E2 or other viral proteins critical for virus reception, cell tropism or viral virulence. The functional significance of E1/E2 heterodimers for reception and infection of target cells in vivo is not known.

Consistent with a possible direct or indirect effect for the altered E1 on virus attachment and/or spread, RB-C22v exhibited a small-plaque phenotype in SK6 cells when compared with parental pBICv. Hulst et al. (2000. *J. Virol.* 74: 9553-9561; 2001. *J. Virol.* 75: 9585-9595) have described heparin sulfate-binding dependent small plaque variants containing mutations in the $E^{ms}$ protein following serial passage of CSFV Brescia in SK6 cells. Notably, these CSFV variants had unaltered virulence phenotypes in pigs (Hulst et al. 2000, 2001, supra). With other Flaviviruses, Japanese Encephalitis Virus (JEV) and Murray Valley Encephalitis Virus (MVEV), cell culture passage selected for variants with a small plaque phenotype increase heparin affinity/sensitivity, and decreased neurovirulence in a mouse model (Lee et al. 2002. *J. Virol.* 76: 4901-4911). Mutations in the E glycoprotein, analogous to the E2 glycoprotein of Pestiviruses, conferred the attenuated phenotype (Lee et al., supra). JEV/MVEV variants failed to exit the peripheral inoculation site (footpad) in mice following infection (Lee et al., supra). It was suggested that viral attenuation may be due to an increase affinity for glycosaminoglycans (GAGs), which prevented viremia by strongly binding variant viruses to proteoglycans on the cell surface and extracellular matrix, thus preventing spread of the virus to the brain. MVEV attenuated mutants with alterations in the E glycoprotein, demonstrated unperturbed binding and penetration rates, suggesting that disruption of E protein function might have resulted from protein structural instability affecting virus infection at a point beyond initial entry into the host cell (Hurrelbrink et al. 2001. *J. Virol.* 75: 7692-7702).

Controlling virus shedding from infected animals is of paramount importance in controlling a disease outbreak. Shedding of the pBICv was absent in animals challenged either at 3, 7, or 21 days post-RB-C22 infection, being present only when challenged at 1 day after RB-C22v infection. These results are comparable to those of Terpstra et al. (1977. *Tijdschr Diergeneeskd* 102: 106-112) and Biront et al. (1987. *Vet Microbiol.* 14: 105-113) showing that vaccination with CSFV strains C or Behring effectively reduced the viral replication in vaccinated pigs.

Neutralizing antibodies have a protective role against CSFV (Coggins, L. 1964. *Am. J. Vet Res.* 25: 613-616; Aynaud and Launais. 1978. *Dev. Biol. Stand.* 41: 381-387; Terpstra et al. 1988. *Vet. Microbiol.* 16: 123-128). Antibodies against CSFV, detected by ELISA and neutralization assays, only appear at significantly high levels at 15 days post RB-C22v infection, reaching their maximum at 21 days. Thus, neutralizing antibody is apparently not likely the major immune effector mechanism involved in the early protection, indicating that antibody-independent mechanisms limit replication of the challenge CSFV. Although the mechanism mediating protection against challenge at 3 days after RB-C22v infection has not been determined, the data presented (see Table 12) suggest that interference with PBIC replication takes place at the tonsil level, as has also been postulated for the early protection mediated with the vaccines strains C or Behring (Terpstra et al. 1977 and Biront et al. 1987, supra). It could be speculated that once RB-C22v reach the tonsils, by 72 h PI, an environment is established that interferes with the local replication and the further generalization of the infection of the challenging pBIC virus. The mechanism mediating this interference is not known. Interferon, or another lymphokine-mediated mechanism as well as perhaps a direct competition for a limited number of target cells could be implicated. On the other hand, cellular immune effector mechanisms preventing virus replication, e.g., activation of natural killer and cytotoxic T lymphocytes, could be responsible for protection, as it has been described in the clearance of other non-cytopathic viruses such as LCMV (Byrne and Oldstone. 1984. *J. Virol.* 51: 682-686; Moskophidis et al. 1993. *Nature* 362: 758-761).

We show that RB-C22v as a candidate to be used as a live attenuated vaccine strain since it (i) induces solid protection status early after its administration, (ii) abrogates shedding of the challenge virus, (iii) contains a genetic marker for attenuation. Additionally, (iv) the 19 amino acid residue insert in E1 can be used as a target for the insertion of an antigenic epitope in order to construct a positively marked antigenic vaccine to differentiate the immune response elicited by naturally-infected and RB-C22v-vaccinated animals.

In addition to the findings characterizing the role of E1 in viral virulence, the role of E2 was evaluated. Chimeras of the Brescia strain and the attenuated vaccine strain CS were constructed. The replacement of the E2 gene in the highly pathogenic strain Brescia with the E2 gene from the vaccine strain CS results in significant in vivo attenuation. Unlike the acute fatal disease induced by Brescia and its infectious clone BICv, infection with the 319.1v chimera was subclinical, characterized by decreased viral replication in tonsils, limited generalization of infection, and reduced virus shedding. The 319.1v attenuation phenotype was independent of its ability to replicate in primary macrophage cell cultures. It is notable that no other CS genome region was able to attenuate the virulent Brescia phenotype, indicating the significance of CS E2 in attenuation.

Specific features responsible for the functional difference of CS E2 are unknown. Comparative sequence analysis of Brescia and CS E2 regions revealed no insertion/deletions and 6% nucleotide divergence over 1119 nucleotides, including 40 synonymous and 22 nonsynonomous substitutions. The 22 predicted amino acid substitutions in CS relative to Brescia are distributed along E2, with only two adjacent positions (238 and 239) affected. Substitutions are generally conservative or neutral, as only six substitutions (T56R, T197M, P200L, S238L, R290S, and L370P) are relatively nonconservative [≦in a normalized PAM250 substitution matrix (Devereux et al. 1984. *Nucleic Acid Res.* 25: 3389-3402)]. Highly conservative I137V and I342V substitutions were present in a previously predicted fusion peptide region (Garry et al. 2003. *Virology* 307: 255-265) and near the strongly predicted carboxyl-terminal transmembrane domain (position 342 to 366) of CS E2, respectively. Few substitutions were found in regions consistently altered in predicted secondary structure, but included K45R, a residue previously affecting domain C antigenicity when experimentally mutated in Brescia (Van Rijn et al. 1994. *J. Virol.* 68:3934-3942), G99E, and notably T197M and P200L, which locally affect hydrophobicity and predicted B-sheet formation in CS E2. Also notable is L370P, a mutation which resulted in loss of a predicted carboxyl-terminal alpha-helical structure in CS E2 and in the reversed transmembrane topology predicted for CS E2.

Attenuation of 319.1v in pigs could conceivably involve some aspect of virus attachment and/or efficiency of entry into critical target cells in vivo. Given that macrophages are targeted in vivo, it is notable that 319.1v exhibited normal growth in macrophage cell cultures in vitro. $E^{ms}$, E1, and E2 are structural glycoproteins in the CSFV virion envelope, and available evidence indicates E2 is an essential gene (van Gennip et al. 2002, supra). Anchored to the envelope, E2 appears as both homo and heterodimers linked by disulfide bridges (Thiel et al., Weiland et al. 1990, Weiland et al. 1999, supra) and, along with $E^{ms}$, is known to be critical for virus reception (Hulst et al. 1997, supra). Pestiviruses containing chimeric E2 proteins have altered host range. Partial replacement of the amino terminus of CSFV E2 with the homologous sequence from BVDV resulted in a virus that, although differing from BVDV in its capacity to infect fetal bovine epithelial cells, resembled BVDV with a 10 fold decrease in its ability to replicate in SK6 cells (van Gennip et al. 2000, supra). Additionally, a chimeric BVDV containing the complete E2 gene of border disease virus (BDV), similar to BVDV, is unable to replicate in MDBK cells, a cell line permissive for BVDV (Lian et al. 2003. *J. Gen. Virol.* 84: 1269-1274).

Consistent with a possible direct or indirect effect for the altered E2 on virus attachment and/or spread, 319.1v exhibited a small-plaque phenotype in SK6 cells when compared with parental BICv. Plaque size was reduced approximately 50%. Interestingly, CSICv also has a reduced plaque size compared with BICv, although in this case reduction was 90%. Thus, additional genetic determinants in the CSICv genome are likely involved in the small plaque phenotype. A correlation between plaque size in vitro and pathogenesis in vivo has yet to be established. Hulst et al. (2000, 2001, supra) serially passaged CSFV Brescia in SK6 cells to generate heparin sulfate-binding dependent small plaque variants that contained mutations in the $E^{ms}$ protein; however, these variants had an unaltered virulence phenotype in pigs.

Despite this data implicating E2 in swine virulence, the presence of additional CSFV virulence determinants outside the E2 region are indicated. All Brescia structural proteins, including E2, when inserted into the CS genetic background were unable to restore a virulent phenotype to CS. This result suggests that CS contains additional mutations affecting virulence in untranslated and nonstructural protein encoding regions. Given the history of CS virus, a vaccine virus safely used for over thirty years (Zaberezhny et al. 1999. *Dtsch Tierarztl Wochenschr* 106: 373-416), it is not surprising that CS may contain additional attenuating mutations which affect multiple proteins. In fact, CS demonstrated 531 nucleotide differences with Brescia across the genome resulting in 105 amino acid substitutions affecting both 5' and 3' untranslated regions and all viral proteins except NS4A (data not shown). Additional support for other contributing virulence determinants is suggested by the somewhat more attenuated phenotype for 138.3v (E2/p7/NS2-3 substitution) relative to 319.1v (E2 substitution only) observed as reduced blood and tissue titers and the absence of generalized infection (Table 4, FIG. 5). Most significantly, any additional CS mutations affecting virulence were unable to attenuate BICv in the context of the chimeras generated here, further highlighting the significance of E2 in swine virulence.

Thus, novel CSFV virulence determinants associated with E1 and E2 glycoprotein function have been identified. Understanding the genetic basis of CSFV virulence and host range will permit rational design of live attenuated CSF vaccines of enhanced safety, efficacy and utility.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Swine kidney cells (SK6) (Terpstra et al. 1990. *Dtsch Tierarztl Wochenschr* 97: 77-79) and free Bovine Viral Diarrhea Virus (BVDV) were used throughout this study. SK6 cells were cultured in Dulbecco's Minimal Essential Medium (DMEM, GIBCO, Grand Island, N.Y.) with 10% fetal calf serum (FCS, Atlas Biologicals, Fort Collins, Colo.). CSFV Brescia strain (obtained from the Animal and Plant Health Inspection Service, Plum Island Animal Disease Center) was propagated in SK6 cells and used for infectious cDNA clone construction. The CS vaccine strain is derived from the LK VNIIVIM parental vaccine strain by serial passages and cloning (Zaberezhny et al., supra). Titrations of CSFV from clinical samples were conducted in 96 well plates (Costar, Cambridge, Mass.) using SK6 cells. After 4 days in culture, viral infectivity was detected by immunoperoxidase assay using the CSFV monoclonal antibody 303 (Edwards et al. 1991. *Vet. Microbiol.* 29: 101-108) and the Vectastain ABC kit (Vector Laboratories, Burlingames, Calif.) (Risatti et al., supra). Titers were calculated according to the method of Reed and Muench (1938. *Amer. J. Hygiene* 27: 493-497) and expressed as TCID50/ml. As performed, test sensitivity was ≧1.8 TCID50/ml. Primary swine macrophage cell cultures were obtained as described by Zsak et al. (1996. *J. Virol.* 70: 8865-8871).

Example 2

Construction of CSFV Brescia pBIC, E1 Mutant RB-C22, E2 CS pCSIC and Chimeric Full-Length cDNA Infectious Clones Total cellular RNA was obtained from SK6 cells (TRIzol method, Gibco) infected with peripheral blood obtained from pigs infected with CSFV strain Brescia or vaccine strain CS. cDNA spanning the entire genome of CSFV Brescia and CS were obtained by reverse transcription (RT) as follows: the reaction [1 µl of MMLV RT buffer, 4 mM dNTPs, 10 pmoles of specific reverse primers R12292, R8538, and R4567 (Table 1), 2 µL of total RNA, and 5.3 µl of water was incubated at 70° C. for 5 min, cooled at room temperature for 20 min, and further incubated for 1 hr at 37° C. following addition of 2 units of MMLV RT (Stratagene, Cedar Creek, Tex.). The entire genome of both strains was PCR amplified in three overlapping fragments using specific primers (Table 1 and FIG. 1A).

Figure 1A:
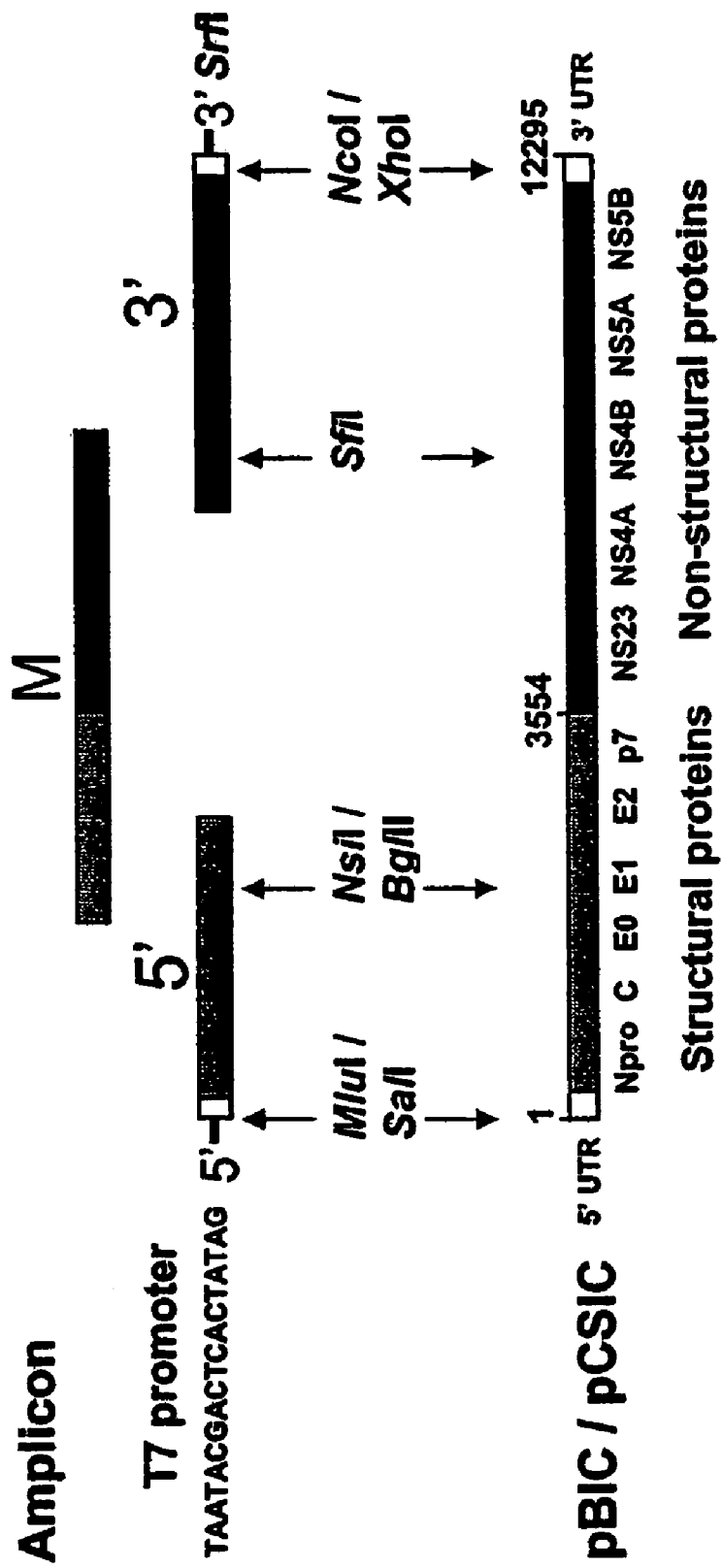
FIG. 1A depicts the construction of CSFV infectious cDNA clones pBIC and pCSIC using amplicon fragments 5', M and 3'. Corresponding restriction sites and nucleotide numbers are shown (pBIC/pCSIC).
Figure 2:
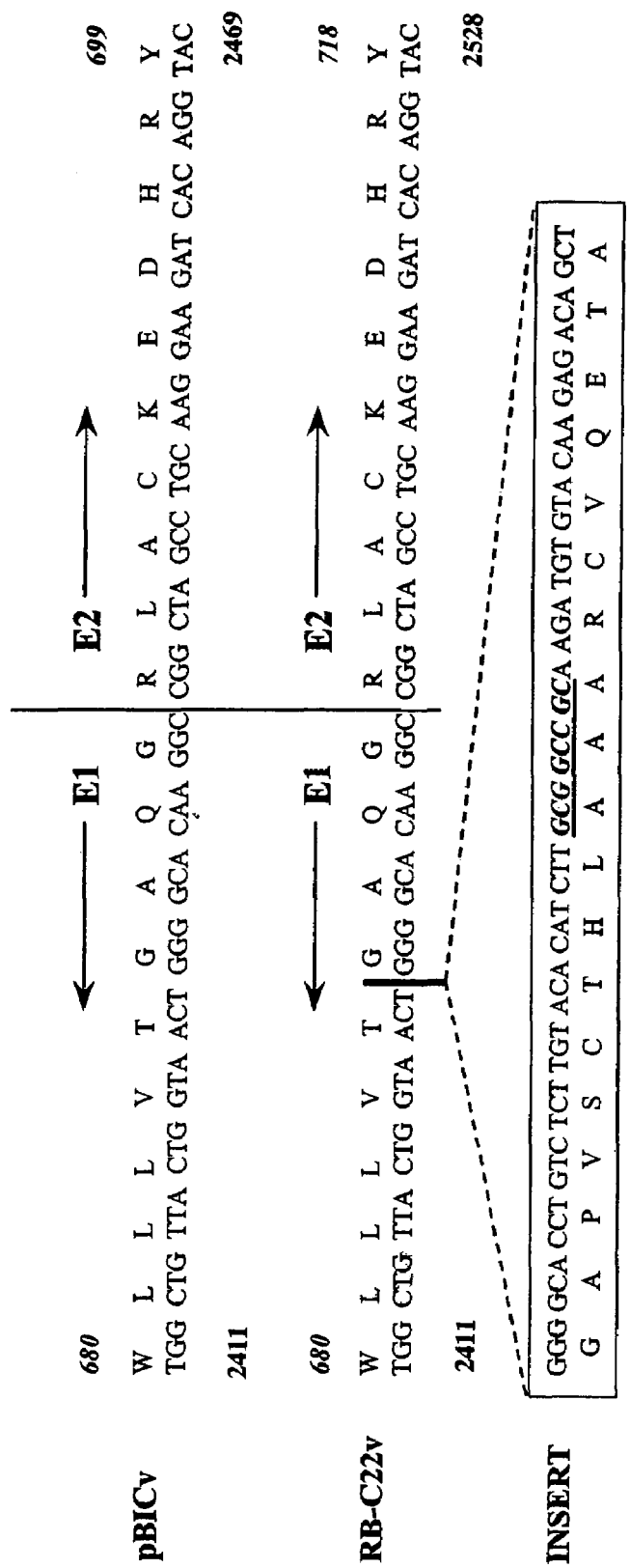
FIG. 2 shows the location of the 19 mer peptide insertion in the E1 glycoprotein and describes the nucleotide and amino acid sequences of the insert present in CSFV RB-C22v. Bold numbers indicate nucleotide position. Numbers in italics indicate amino acid residue position. Underlined letters in bold italics represent the NotI restriction site in the transposon insert. The nucleotide sequences of pBicv, RB-C22v, and the 19 mer insertion are identified by SEQ ID NOs: 25, 25, and 27, respectively. The amino acid sequences of pBicv, RB-C22v, and the 19 mer insertion are identified by SEQ ID NOs: 26, 26, and 28, respectively. The SEQ ID NO: of the nucleic acid encoding the E1 glycoprotein comprising the 19 mer insertion is SEQ ID NO:29; the polypeptide sequence is identified by SEQ ID NO:30.

Infectious RNA was in vitro transcribed from a full-length copy of CSFV strain Brescia or CS (FIG. 1A). cDNA of the viral genome was amplified by RT-PCR using specific primers (Table 1) and cloned into the low copy number plasmids pACYC177GR and pACYC177AZ (Table 1) to obtain PBIC and pCSIC, full-length DNA copies of the Brescia and CS viral genomes, respectively (FIG. 1A). RNA transcripts were obtained from these plasmids and used to transfect SK6 cells. Virus was rescued from transfected cells at day 4 post-transfection. Nucleotide sequences of the rescued virus BICv/CSICv genomes were identical to parental viruses Brescia and CS, respectively.

A 4.3 Kb fragment encompassing the 3' end of CSFV genome was amplified by semi-nested PCR using primer combination F8017-Bresia3' (Brescia virus) or F8017-CS3' (CS virus), then re-amplified with primer combination F8210-Bresia3' or CS3'. The amplified DNA fragments were excised from a 1% agarose gel and cloned using SfiI/NcoI sites (Brescia virus) or SfiI/XhoI sites (CS virus) into pACYC117GR and pACYC117AZ (see below) to obtain plasmids pBrescia 3' end or pCS 3' end, respectively.

A 4.8 Kb fragment encompassing the middle part of the CSFV Brescia genome was amplified using primer combination F3237-R8127 (Brescia virus) or F2008-R8127 (CS virus). The amplified fragments were purified as above, then cloned into pCR4Blunt using a Topo cloning kit (Invitrogen, San Diego, Calif.) to create the plasmid pTOPOBmiddle (Brescia virus) or pTOPOCSmiddle (CS virus). pTOPOBmiddle was then digested with NsiI-SfiI and the fragment cloned into pACYC177GR to create the plasmid pBrescia middle. Similarly, pTOPOCSmiddle was BglII-SfiI digested and the fragment cloned into pACYC177AZ to generate the plasmid pCSmiddle.

A 3.1 Kb amplicon encompassing the 5' end area of the CSFV genome was amplified using primers Brescia 5' and R3126 (Brescia virus) or CS 5' and R3668 (CS virus). Amplified products were cloned in pCR4Blunt as above to generate plasmid vectors pTOPOB5' end and pTOPOCS5' end. pTOPOB5' end was digested with MluI-NsiI and the fragment cloned into pBresciamiddle to generate the vector pBresciamiddle-5' end. pBrescia-3' end was digested with SfiI-SacII and the fragment cloned into pBresciamiddle-5' end to generate a full-length plasmid pBIC (FIG. 1A). Similarly, pTOPOCS5' end was SalI-BglII digested and cloned into pCSmiddle to generate the vector pCSmiddle-5'end. pCS3' end was SfiI/XhoI digested and cloned into pCSmiddle-5' end to generate a full-length plasmid pCSIC (FIG. 1A).

The low copy plasmids used here, pACYC177GR and pACYC177AZ, are pACYC177 derivatives (New England Biolabs, Beverly, Mass.), obtained by removing a 1.2 Kb AatII-XhoI from pACYC177 and replacing it with a synthetic oligonucleotide containing unique restriction sites (Table 1).

TABLE 1

Oligonucleotides used in the construction of pBIC, pCSIC, and chimeric p138, p319.1, and p312.1 infectious clones.

| Primer | Sequence[a] | Function | SEQ ID NO: |
|---|---|---|---|
| MCSF Brescia | 5'ACGTCACTAGTC*ACGCGT*AT*ATGCAT*AT*GGCC GTAGCGGCC*AT*CCATGG*CTCGA3' | Multiple Cloning site | 1 |
| MCSR Brescia | 5'CACTAGTC*ACGCGT*AT*ATGCAT*AT*GGCCTAGC GGCC*AT*CCATGG*C | Brescia | 2 |
| R4567 | 5'CTCCTGCTATTTCATCTA3' | RT[c] 5' end | 3 |
| Brescia 5'[b] | 5'ACTAGT*ACGCGT*TAATACGACTCACTATAG TATACGAGGTTAGTTCA3' | PCR[d] 5' end | 4 |
| CS5' | 5'GTCAGTCGACTTAATACGACTCACTATAGTA TACGAGGTTAGTTCA3' | PCR 5' end | 5 |
| R3534B | 5'GCGAGTTGTTCTGTTAGA3' | PCR 5' end | 6 |
| R3668 | 5'ATCCATTTCTTTATAGGC3' | PCR 5' end | 7 |
| R8538 | 5'CCCTATCCTATCATCCGT3' | RT middle | 8 |
| R8127 | 5'GTGTTCTCTTCTGCTCAC3' | PCR middle | 9 |
| F3007 | 5'GGG GGG CAA TTG GAC ATG3' | PCR middle | 10 |
| R12292 | 5'GGG CCG TTA GAA ATT ACC TTA3' | RT 3' end | 11 |
| Brescia 3' | 5'ATTG*CCATGGCCCGGGCC*CGTTAGAAATTACCT TA3' | PCR 3' end | 12 |
| F8017 | 5'AAGCGATGGTTTGCTAGG3' | PCR 3' end | 13 |
| F2379 | CCTCATCTGCTTGATAAAAG | p138.8 | 14 |
| R6636 | CCTTCTCTGGGCTTGTTC | p138.8 | 15 |
| FSacII | 5'GAACAACTCGCCGCGGGTCTACAGTTAGG3' | SacII site | 16 |
| RSacII | 5'CCTAACTGTAGACCCGCGGCGAGTTGTTC3' | SacII site | 17 |
| MCS+ | 5'CCGGCCGCGTCGACATAGATCTAT*GGCCG TAGCGGCC*3' | CS Multiple cloning site | 18 |

TABLE 1-continued

Oligonucleotides used in the construction of pBIC, pCSIC, and chimeric p138, p319.1, and p312.1 infectious clones.

| Primer | Sequence[a] | Function | SEQ ID NO: |
|---|---|---|---|
| MCS– | 5'TCGAGGCCGCTACGGCCATAGATCTATGTC GACGCGGCCGGACGT3' | | 19 |
| F2008 | 5'GATTCTCCATGAGATGGG3' | PCR middle | 20 |
| CS3' | 5'ATTGCTCGAGCCCGGGCCGTTAGGAAATT ACCTTA3' | PCR 3' end | 21 |
| F8210 | 5'GATGAATTAGTCAAGGAG3' | PCR 3' end | 22 |
| F3237 | 5'ACACAACTGTCAAGGTGC3' | PCR middle | 23 |
| R3126 | 5'TCTGTAACCTGTCTCATT3' | PCR 5' end | 24 |

[a]The restriction sites are depicted in bold, italics, underlined fonts, from 5' to 3'.
For MCSF Brescia: Mlul, Nsil, Sfil, and Ncol.
For Brescia 5': Mlul.
For Brescia 3': overlapping Ncol and Sfil.
[b]Bold letters indicate the T7 promoter
[c]RT: reverse transcription
[d]PCR: polymerase chain reaction; 5' end, middle, and 3' end are amplicons (FIG. 1A).

Mutated cDNA clones were produced by random insertions of a 19 amino acid linker using transposon linker insertion mutagenesis and a Tn insertion kit (Epicentre Technologies, Madison, Wis.) according to manufacturer's instructions. Mutagenized clones were selected in the presence of kanamycin. Selected clones were sequenced using transposon specific primers to locate insert position. The 1.4 Kb insert was then removed using NotI, linearized clones were excised from the gel and ligated using T4 DNA ligase (New England Biolabs), and transformed into TOP 10 E. coli (Invitrogen). Transformed bacteria that grew in the presence of ampicillin but not in the presence of kanamycin were further selected and sequenced with CSFV Brescia specific primers to determine the position of the 57 nt insert (SEQ ID NO: 27). Plasmids bearing inserts at desired positions were used in in vitro transcription reactions to transfect SK6 cells. Among other mutants, RB-C22v, containing the 57-nucleotide in frame insertion at nt position 2429, in the carboxyl end of glycoprotein E1, was selected for further characterization (FIG. 2). The 19-codon insertion was located four residues upstream of the cleavage site between envelope glycoproteins E1 and E2 (FIG. 2). The complete nucleotide sequence of RB-C22v was obtained and compared with that of pBICv. Nucleotide sequences for both viruses were identical with the exception of the presence of the 57-nucleotide insertion at position 2429 in RB-C22v.

Figure 3:
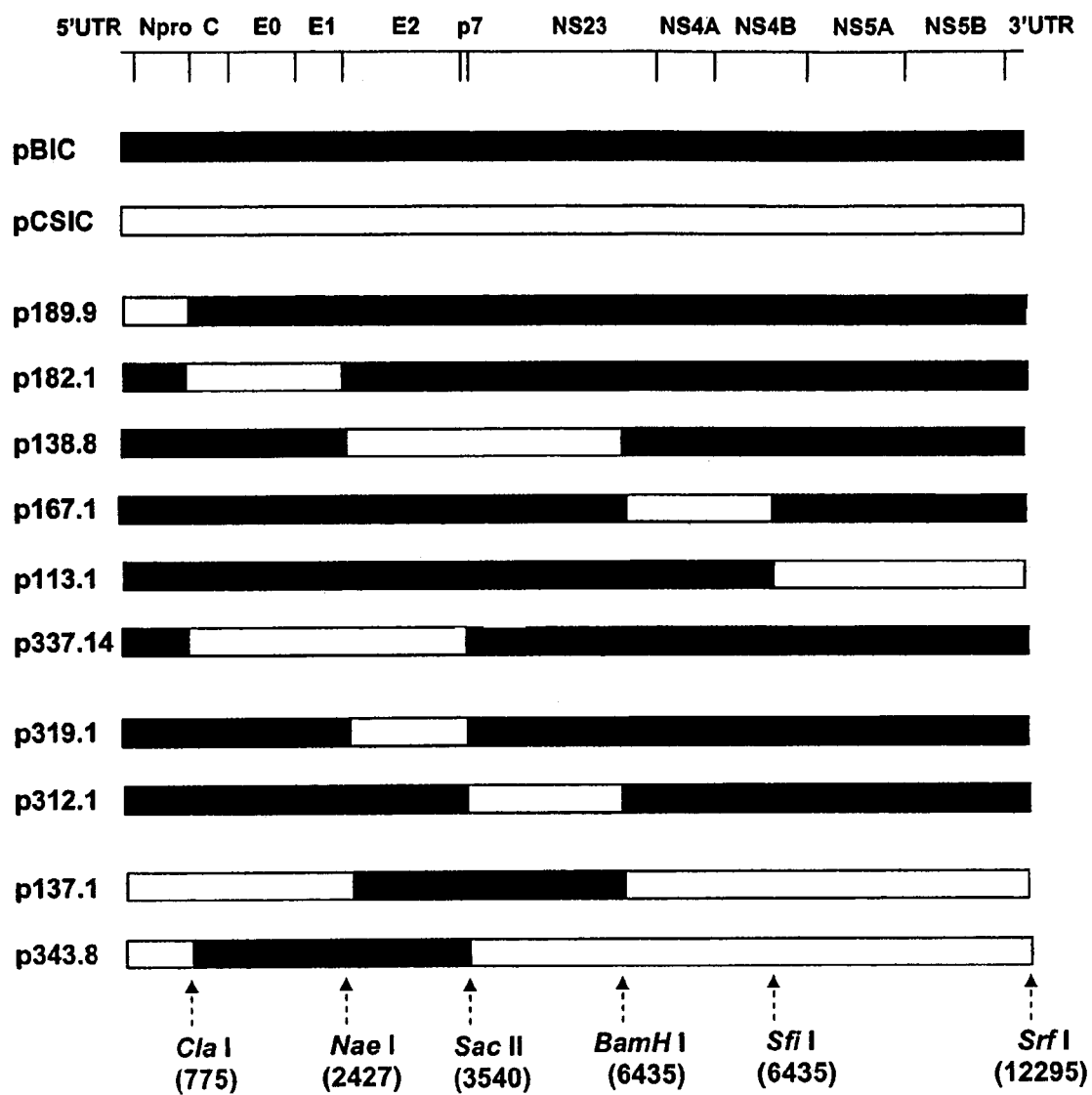
FIG. 3 depicts the construction of CSFV chimeric viruses. Corresponding restriction sites and nucleotide numbers are depicted.

Chimeric cDNA infectious clones p189.9, p182.1, p138.8, p167.1, p113.1 and p337.14 were constructed by replacing, respectively, the restriction fragments ClaI-SrfI, ClaI-NeaI, NeaI-BamHI, BamHI-SrfI, SrfI-SrfI, and ClaI-SacII in pBIC with the homologous fragment from the CS strain (FIG. 3). Chimeric cDNA infectious clones p137.1 and p343.8 were constructed by replacing, respectively, the restriction fragments NeaI-BamHI and ClaI-SacII in PCs with the homologous fragment from PBIC (FIG. 3).

Chimeric cDNA infectious clones p319.1 and p312.1 were constructed as follows. The NeaI-BamHI fragments from pBIC and pCSIC were obtained by PCR using the primers F2379 and Rcc36 and cloned using a TA Topo kit (Invitrogen) to create the plasmids pTOPOBreN/B and pTOPOCSN/B, respectively. These plasmids were used as targets for site directed mutagenesis using the QuikChange XL kit (Stratagene) and the specific oligonucleotide primers FSacII and RSacII, complementary to each strand of the target. Following mutagenesis, the reaction was treated with 10 U of endonuclease DpnI to eliminate methylated target DNA, and extended products were transformed into XL10 Gold ultra competent cells (Stratagene). DNA obtained from the transformants was purified (QIAGEN Plasmid kits, Valencia, Calif.) and sequenced to verify the presence of the desired mutation. Extension resulted in creation of a SacII site and introduction of a silent mutation at position 3540 to yield the following plasmids, pTOPOBreN/BSacII and pTOPOCSN/BSacII. NeaI-SacII fragments of each plasmid containing the genomic region E2/p7-NS2-3 were reciprocally interchanged, creating the chimeric plasmids pTOPO-BreCS and pTOPOCSBre (Brescia/CS and CS/Brescia, respectively). Finally, the NeaI-BamHI fragment from pTO-POBreCS and pTOPOCSBre were cloned in pBIC to create cDNA infectious clones p319.1 and p312.1, respectively (FIG. 3).

Example 3

Rescue of CSFV Brescia, BICv, CSICv, and Chimeras

Full-length genomic infectious clones were linearized with SrfI and in vitro transcribed using the T7 Megascript system (Ambion, Austin, Tex.). RNA products were precipitated with LiCl and transfected into SK6 cells by electroporation at 500 volts, 720 ohms, 100 watts with a BTX 630 electroporator (BTX, San Diego, Calif.). Cells were plated in 12 well plates and 25 cm² flasks, and incubated for 4 days at 37° C. 5% $CO_2$ atmosphere. Virus was detected by immunoperoxidase staining using a CSFV E2 specific monoclonal antibody (WH303). Stocks of rescued viruses were stored at −70° C. Insert location was confirmed by RT-PCR and sequence analysis.

Example 4

Sequencing

Full-length infectious clones, in vitro rescued viruses, and viruses recovered from infected animals were completely sequenced with CSFV specific primers by the dideoxynucleotide chain-termination method (Sanger et al. 1977. *Proc. Natl. Acad. Sci. USA* 74: 5463-5467). Sequencing reactions were prepared with the Dye Terminator Cycle Sequencing Kit (Perkin-Elmer, Boston, Mass.). Reaction products were sequenced on a PRISM 3700 automated DNA Sequencer (Applied Biosystems, Foster City, Calif.). Sequence data were assembled with the Phrap software program, with confirmatory assemblies performed using CAP3 (Huang et al. 1999. *Genome Res.* 9: 868-877). The final DNA consensus sequence represented on average eight-fold redundancy at each base position. Brescia and CS genomic sequences were deposited in GeneBank under accession nos. AY578687 and AY578688, respectively.

Nucleotide and amino acid comparisons and alignments were done using Blast (b12seq) (Altschul et al. 1997. *Nucleic Acid Res.* 25: 3389-33402) and clustral (Thompson et al. 1997. *Nucleic Acid Res.* 24: 6876-6882). Sequences of the genomes of rescued virus pBICv and wild type CSFV Brescia were identical. Protein characterization and secondary structure predictions (Chou-Fasman and Garnier-Osguthorpe-Robson) were done using MacVector (Accelrys, Inc.) and GCG (Devereuz et al. 1984. *Nucleic Acid Res.* 12: 387-395) software packages, SAPS (Brendel et al. 1992. *Proc. Natl. Acad. Sci. USA* 89: 2002-2006), memsat (Jones et al. 1994. *Biochemistry* 33: 3038-3049) and psipredict (Jones, D. T. 1999. *J. Mol. Biol.* 292: 195-202).

Example 5

In Vitro and In Vivo Analysis of CSFV pBIC and E1 Mutant RB-C22

Figure 1B:
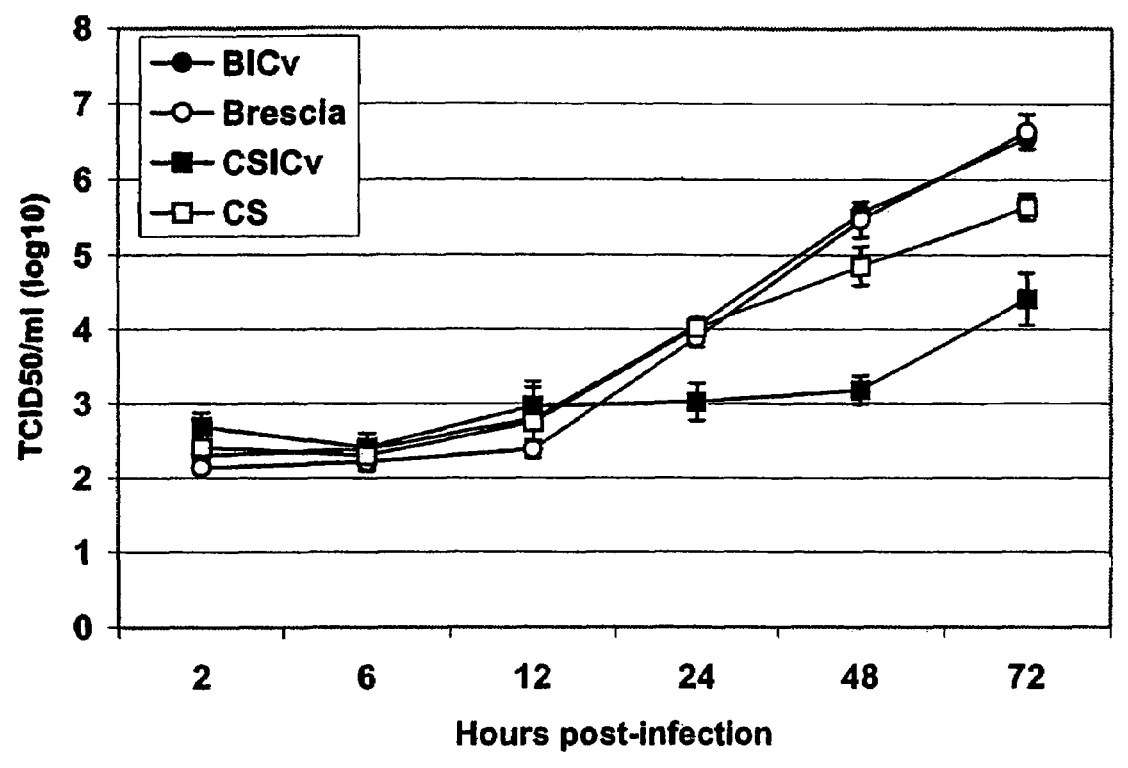

Growth kinetics of pBICv and CSICv were compared with their parental viruses Brescia and CS in a multistep growth curve. Primary porcine macrophage cell cultures were infected at a multiplicity of infection (MOI) of 0.1 $TCID_{50}$ per cell. Virus was adsorbed for 1 h (time zero) and samples were collected at times post infection through 72 or 96 h. Replication kinetics and virus yields between the parental Brescia and its IC-derived virus, BICv were indistinguishable (FIG. 1B). However, CSICv titers were approximately 10-fold lower than parental CS virus (FIG. 1B). To assess pig virulence phenotypes, three pigs were inoculated intranasally with $10^5$ $TCID_{50}$ of parental (Brescia and CS) or infectious clone-derived viruses (pBICv and CSICv). No significant differences in time to onset of clinical disease, mortality rate (which was 100%) time to death, or viremia titers were observed for Brescia and BICv infected animals (Table 2). Animals inoculated with CS or CSICv were free of CSFV-related clinical signs during the experimental period (data not shown). These data indicate that the infectious clone generated viruses, pBICv and CSICv, have parental phenotypes in vitro and in vivo.

TABLE 2

Swine survival, viremia, and fever response following infection with CSFV Brescia (wild type) or the virus derived from infectious clone pBIC (pBICv).

| Virus | Survivors/total | Mean time to death: Days ± SD | Mean time of fever onset: Days ± SD | Mean time of fever duration: Days ± SD |
|---|---|---|---|---|
| Brescia | 0/3 | 13.0 (3.5) | 4.3 (0.6) | 7.0 (1.7) |
| pBIC | 0/3 | 15.3 (2.1) | 5.3 (0.6) | 9.6 (4.2) |

Figure 4B:
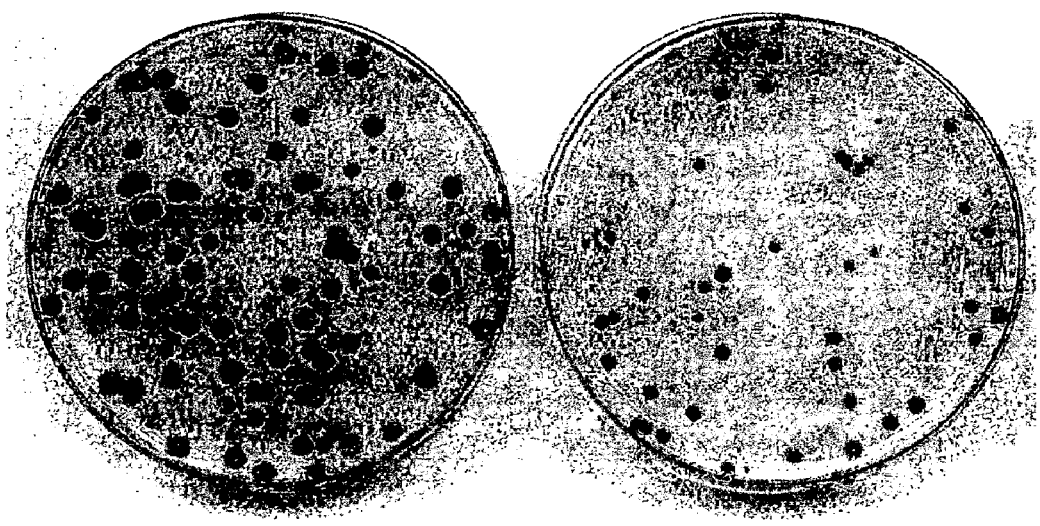
FIG. 4B shows plaque formation of CSFV pBICv and RB-C22v on SK6 cell cultures. Cell cultures were infected with approximately 75

Growth characteristics of RB-C22 and pBIC viruses were compared in a multistep growth curve by infecting primary swine macrophage cell cultures (MOI=0.1) and determining titers for both at various times post-infection. Growth characteristics of RB-C22v and PBIC were indistinguishable (FIG. 4A). Notably, the plaque size of RB-C22v on macrophage and SK6 cell cultures was significantly reduced, by approximately 50%, when compared to PBIC (FIG. 4B).

Immunoprecipitation studies using an anti-E1 rabbit antiserum (raised against a synthetic peptide representing E1 residues 152 to 165) demonstrated equivalent amounts and unaltered electrophoretic mobility of E1 in RB-C22v and pBICv infected cells (data not shown).

Example 6

Differential Detection of RB-C22v and pBIC by RT-PCR

RT-PCR was set to assess the presence of RB-C22v and pBICv in clinical samples and tissues from inoculated pigs. Briefly, total RNA was isolated from samples using RNAeasy columns (Quiagen, Calif.) according to the manufacturer's directions. cDNA synthesis was done using Moloney Murine Leukemia Virus (MMLV) reverse transcriptase (Stratagene) and primer R3126 (TCTGTAACCTGTCT-CATT) in a 10 µl reaction containing primer, dNTP, 10× reaction buffer, and enzyme and incubated for 1 h at 37° C. A 50 µl PCR reaction containing 5 µl of 10×PCR Advantage buffer (Becton Dickenson, Palo Alto, Calif.), 200 nM of each dNTPs (Roche), 10 pmoles of each primer (forward primer: 5'TCATCAGTCTGGAATGT; and reverse primer: 5'GTCATCCCCCATTTCCTC), 2.5 units Advantage DNA polymerase (BD) and 2 µl of cDNA. Cycling conditions were 95° C. 1 min, followed by 35 cycles of 95° C. 20 sec, 52° C. 20 sec, and 68° C. 1 min, then 68° C. 5 min. Amplicons were resolved in a 2% agarose gel stained with ethidium bromide (FIG. 5).

Example 7

Animal Infections

Forty-pound pigs (n=28) aged 10 to 12 weeks old were randomly allocated into three groups. Pigs were intranasally inoculated with $10^5$ $TCID_{50}$ of pBICv (group 1, n=17), RB-C22v (group 2, n=26), or mock infected (group 3, n=2). Clinical signs (anorexia, depression, fever, purple skin discoloration, excessive tear production, staggering gait, diarrhea and cough) were observed daily throughout the experiment. Following inoculation, pigs were sacrificed as follows: group 1, 2 pigs at 2, 4, 6, 9, 11, and 16 days post-infection (DPI); group 2, 3 pigs at 2, 4, 6, 9, 11, and 16 DPI; and group 3, 2 pigs at day 0. Eight animals in groups 1 and 2 were monitored throughout the experimental period (21 days). Complete blood, serum, nasal swabs and tonsil scrapings were obtained from pigs at necropsy. Tissue samples (tonsil, mandibular lymph node, spleen, kidney, liver, mesenteric lymph node, and bone marrow) were snap frozen in liquid nitrogen for virus titration and fixed in 10% neutral buffered formalin for histopathological studies. Blood was obtained from the anterior vena cava in EDTA containing tubes (Vacutainer). Total white blood cell, lymphocyte and platelet counts were obtained using a Beckman Coulter AcT (Beckman, Coulter, Calif.).

Tissue samples were fixed in 10% neutral buffered formalin, embedded in paraffin, and sectioned. Tissue sections were allowed to adhere to Superfrost/plus slides (Fisher Scientific, Pittsburgh, Pa.), heated for 20 min at 65° C., and then deparaffinized using xylene. Sections were rehydrated through a graded alcohol series and washed with phosphate-buffered saline (PBS, pH 7.4). Immunohistochemistry was performed as described by Sur et al. (1996. *J. Clin. Microbiol.* 34: 2280-2286). Briefly, 4 µm sections were first treated with 3% hydrogen peroxide in PBS for 20 min, followed by washes in PBS and digestion with 0.05% Protease XIV (Sigma Chemical Co., St. Louis, Mo.) for 2 min at 37° C. After several washes with PBS, sections were incubated in blocking solution (5% normal goat serum in PBS) for 30 min at room temperature and then incubated for 2 h at 4° C. with CSFV-specific monoclonal antibody directed against E2 glycoprotein (Edwards et al., supra) diluted 1:500 in PBS. Following PBS washes, slides were incubated with alkaline phosphatase-conjugated, goat anti-mouse antibody for 20 min at room temperature.

Mutation of E1 affects CSVF virulence in pigs. The disease pattern observed for RB-C22v-infected animals contrasted markedly with that seen following infection with pBICv. In contrast with pBICv, where mortality was 100%, all RB-C22v-infected animals survived infection (Table 3). RB-C22v-infected animals remained clinically normal following infection (with the exception of a transient hyperthermia in half of the infected animals); whereas, animals infected with pBICv presented clinical signs of CSFV, 3 to 7 DPI, with symptoms progressing until death (Table 3). Blood lymphocytes and platelet number dropped drastically in pBICv-infected animals, at 4-6 DPI, and remained low until death, while in the RB-C22-infected animals only a transient and much less dramatic effect was observed (FIGS. 6A and 6B). Both mean and maximum viremia titers of RB-C22v-infected animals were significantly reduced by $10^2$ to $10^7$ $\log_{10}$ from control values during the acute disease period (Table 4). Additionally, RB-C22v titers in nasal swabs and tonsil scrapings were significantly decreased (10 to 1000 fold; Table 4). These results demonstrate that RB-C22v is markedly attenuated for swine.

TABLE 3

Swine survival, viremia and fever response following infection with CSFV pBICv or RB-C22 viruses.

| Virus | Survivors/total | Mean time to death | Mean time of fever onset Days (±SD) | Mean time of fever duration | Max Daily Temp. |
|---|---|---|---|---|---|
| RB-C22 | 10/10 | — | 5.5 (1.0) | 0.7 (0.8) | 104.1 (0.6) |
| pBIC | 0/10 | 9.12 (3.09) | 4.4 (0.8) | 4.6 (0.8) | 106.1 (0.5) |

TABLE 4

Virus titers in tissues following infection with CSFV pBICv or RB-C22v.

| Tissue | DPI | pBICv | RB-C22v |
|---|---|---|---|
| Nasal swabs | 2 | ≦1.80 | ≦1.80 |
|  | 4 | ≦1.80 | ≦1.80 |
|  | 6 | 2.30 ± 1.15 | 1.85 ± 0.19 |
|  | 9 | 4.47 ± 1.15 | 1.84 ± 0.29 |
|  | 11 | ND | ≦1.80 |
|  | 16 | ND | ≦1.80 |
| Tonsil scrapings | 2 | ≦1.80 | ≦1.80 |
|  | 4 | 2.79 ± 0.26 | 1.92 ± 0.03 |
|  | 6 | 2.00 ± 0.08 | ≦1.80 |
|  | 9 | 4.47 ± 0.19 | ≦1.80 |
|  | 11 | ND | ≦1.80 |
|  | 16 | ND | ≦1.80 |
| Tonsils | 2 | 1.40 ± 1.40 | ≦1.80 |
|  | 4 | 5.55 ± 0.75 | 3.19 ± 0.53 |
|  | 6 | 6.80 ± 0.17 | 5.58 ± 0.23 |
|  | 9 | 7.71 ± 0.09 | 1.97 ± 0.17 |
|  | 11 | 7.80 ± 0.00 | 1.76 ± 0.39 |
|  | 16 | ND | 1.89 ± 0.12 |
| Blood | 2 | ≦1.80 | ≦1.80 |
|  | 4 | 3.11 ± 0.34 | 2.09 ± 0.32 |
|  | 6 | 6.50 ± 0.27 | 2.81 ± 0.75 |
|  | 9 | 9.02 ± 0.28 | 1.84 ± 0.08 |
|  | 11 | ND | ≦1.80 |
|  | 16 | ND | ≦1.80 |
| Mandibular Lymph Node | 2 | ≦1.80 | ≦1.80 |
|  | 4 | 4.05 ± 0.08 | 1.86 ± 0.10 |
|  | 6 | 5.55 ± 0.25 | 2.58 ± 0.92 |
|  | 9 | 7.47 ± 0.34 | ≦1.80 |
|  | 11 | 7.80 ± 0.00 | ≦1.80 |
| Brain | 16 | ND | ≦1.80 |
|  | 2 | ≦1.80 | ≦1.80 |
|  | 4 | ≦1.80 | ≦1.80 |
|  | 6 | 5.05 ± 1.08 | ≦1.80 |
|  | 9 | 4.64 ± 0.84 | ≦1.80 |
|  | 11 | 6.80 ± 0.00 | ≦1.80 |
|  | 16 | ≦1.80 | ≦1.80 |
| Spleen | 2 | ≦1.80 | ≦1.80 |
|  | 4 | 2.14 ± 1.17 | ≦1.80 |
|  | 6 | 5.97 ± 0.00 | 1.97 ± 0.00 |
|  | 9 | 7.47 ± 0.34 | 1.86 ± 0.10 |
|  | 11 | 7.80 ± 0.00 | ≦1.80 |
|  | 16 | ND | ≦1.80 |
| Mesenteric Lymph Node | 2 | ≦1.80 | ≦1.80 |
|  | 4 | 2.14 ± 0.47 | 2.14 ± 0.16 |
|  | 6 | 5.64 ± 0.17 | 2.58 ± 0.24 |
|  | 9 | 7.55 ± 0.25 | ≦1.80 |
|  | 11 | 7.80 ± 0.00 | ≦1.80 |
|  | 16 | ND | ≦1.80 |
| Kidney | 2 | 2.47 ± 0.67 | ≦1.80 |
|  | 4 | 1.80 ± 0.00 | ≦1.80 |
|  | 6 | 4.47 ± 0.17 | ≦1.80 |
|  | 9 | 7.22 ± 0.42 | ≦1.80 |
|  | 11 | 7.47 ± 0.00 | ≦1.80 |
|  | 16 | ND | ≦1.80 |
| Bone Marrow | 2 | ≦1.80 | ≦1.80 |
|  | 4 | 3.05 ± 0.08 | 1.97 ± 0.17 |
|  | 6 | 7.63 ± 0.00 | 3.08 ± 0.78 |
|  | 9 | 7.87 ± 0.07 | 1.97 ± 0.17 |
|  | 11 | 6.99 ± 0.00 | ≦1.80 |
|  | 16 | ≦1.80 | ≦1.80 |

For a more detailed comparison of RB-C22 and pBIC pathogenesis, randomly selected animals were euthanized at 2, 4, 6, and 8 DPI (two animals/time point/group), and tissue samples were collected for virus titration, histopathological and immunohistochemical analysis.

Virus tissue titers are shown in Table 4. RB-C22v replication in tonsils was significantly decreased (between $10^2$ to $10^7$ $\log_{10}$, depending on time PI) compared with pBICv. At 4 to 6 DPI, RB-C22v was isolated from the draining submandibular lymph node at titers that were 100 to 1000 fold lower than those observed for the pBIC-infected animals. Generalization of infection occurred in both, RB-C22v- and pBICv-infected animals by 4 DPI. However, at this and all later time points, RB-C22v titers in spleen, liver, kidney, and mesenteric lymph node were significantly lower (approximately $10^2$ to $10^3$ $\log_{10}$) than values observed for pBICv-infected animals. Interestingly, central nervous system (CNS) involvement in RB-C22v-infected animals was markedly reduced. In contrast, titers of $10^5$ to $10^6$ $TCID_{50}$/gram were present in CNS tissues of pBIC-infected animals. Overall, RB-C22v infection resulted in reduced generalization of infection and significantly lower tissue titers.

Histological lesions in pigs inoculated with pBICv were observed as early as 4 DPI. These included tonsillar and submandibular lymphoid necrosis and depletion, which progressed to abscess formation by 10 DPI. Additionally, between 6 to 10 DPI, there was moderate to marked histiocytic hyperplasia and reticuloendothelial cell proliferation. RB-C22v-infected pigs showed similar pathology of the tonsil and regional submandibular lymph node but the degree was markedly reduced with a minimal to mild lymphoid necrosis and only a mild histiocytosis. Notably, in these animals lesions began to resolve with evidence of lymphoid hyperplasia by 11 DPI. PBICv-infected spleen was characterized by moderate to severe lymphoid follicular depletion, necrosis and mild to moderate histiocytosis, while in RB-C22v-infected pigs there were negligible changes in the spleen with minimal lympholysis and depletion. As early as 6 DPI, pBICv-infected pigs had a moderate to marked meningoencephalitis with vasculitis and prominent perivascular lymphohistiocytic cuffs. In those animals, at 10 DPI, cerebral and cerebellar necrosis were associated with severe vasculitis and thrombosis. In contrast, in CNS of the RB-C22v-infected pigs, there was minimal pathology characterized by rare perivascular cuffs of a few lymphocytes and macrophages and foci of gliosis, in only 7 of 18 animals.

The presence of CSFV antigen in tissues of infected animals was consistent with the degree and distribution of lesions and virus tissue titers. In pBICv-infected pigs there was antigen in superficial and cryptic tonsillar epithelial cells and tonsillar endothelium by 2DPI. At 4DPI, antigen was observed in tonsillar macrophages and lymphoid follicles with moderate to marked immunoreactivity. In these animals a similar immunoreactivity was observed in mandibular lymph node and the spleen, which included macrophages and endothelium. In the brain of the pBICv-infected animals there was CSFV antigen labeling by 2DPI with moderate to marked immunoreactivity by 6 DPI in vascular endothelium, perivascular macrophages and in glial cells, the later more pronounced at 10 DPI. With RB-C22v-infected pigs the highest immunoreactivity was observed in tonsils, with a significant reduction of staining in the submandibular lymph node, spleen and brain. In the brain, minimal reactivity was observed in only 4 of 18 animals and was associated with perivascular macrophages while no CSFV antigen was observed in the cells.

The data presented indicate that mutation of glycoprotein E1 affects pig virulence. RB-C22v infection is characterized by an absence of clinical disease, decreased viral replication in tonsils, limited generalization of infection, and dramatic reduced virus shedding.

Example 8

Chimeric Viruses Indicate CSFV E2 is a Virulence Determinant in Pigs

Initial screening of chimeric viruses 189.9v, 182.1v, 138.8v, 167.1v, 113.1v, 337.14v, 137.1v, and 343.8v to determine a virulence phenotype was conducted by intranasal inoculation of two 10 to 12 week old pigs $10^5$ TCID$_{50}$ of each virus. Clinical signs and temperature were observed daily as described in Example 7. More detailed pathogenesis studies with attenuated chimeric viruses 138.8v, 319.1v, and 312.1v were conducted with similar pigs (n=30) randomly allocated into 5 groups of 6 animals each. Pigs were intranasally inoculated with $10^5$ TCID$_{50}$ of BICv, CSICv, or chimeric viruses. Clinical signs were observed daily throughout the experiment and scored as previously described (see Example 7). One pig per group was necropsied at 6 and 8 DPI, at which time blood, serum, nasal swabs, and tonsil scraping samples were obtained. Tissue samples were fixed and analyzed as in Example 7. Tissue samples (tonsil, mandibular lymph node, and spleen) were snap frozen in liquid nitrogen for virus titration or fixed in 10% neutral buffered formalin for histopathological studies. Blood was obtained from the anterior vena cava in EDTA-containing tubes (Vacutainer). Total white blood cell, lymphocyte and platelet counts were obtained using a Beckman Coulter AcT (Beckman, Coulter, Calif.).

Only two chimeras, 138.8v and 337.14v, exhibited the attenuated phenotype of CSICv, while the other four chimeras exhibited the virulence phenotype of parental BICv (Table 5). The CS region common to both 138.8v and 337.14v encoded the E2 gene, suggesting a significant virulence determinant absent in CS E2 was responsible for attenuation of these chimeras.

TABLE 5

Swine survival, clinical scores and fever response following infection with BICv, CSICv, and chimeric viruses.

| Virus | # Survivors/Total | Mean time to Death-Days | Fever Days to Onset | Fever Duration |
| --- | --- | --- | --- | --- |
| BICv | 0/10 | 9.1 (3.1) | 4.4 (0.8) | 4.6 (0.8) |
| CSICv | 4/4 | — | — | — |
| 189.9v | 0/4 | 8.75 (2.6) | 3 (0) | 5.2 (3.2) |
| 182.1v | 0/2 | 11.5 (6.4) | 4 (0.7) | 5.5 (4.9) |
| 138.8v | 2/2 | — | 8.5 (0.5) | 1 (0) |
| 167.1v | 0/2 | 12 (4.65) | 6.5 (0.7) | 9 (2.8) |
| 113.1v | 0/2 | 8 (0) | 4 (0) | 4 (0) |
| 337.14 | 2/2 | — | — | — |
| 137.1v | 2/2 | — | — | — |
| 343.8v | 2/2 | — | 8[a] | 1 |

[a]Only one animal showed fever for 1 day

To confirm the role of E2 in swine virulence and further map the region responsible for 138.8v attenuation, two additional chimeric viruses, 319.1v and 312.1v were constructed to contain CS regions encoding E2 only or p7 and the amino terminal 894 amino acid residues of NS2-3, respectively (FIG. 3). Chimeric viruses were rescued and their nucleotide sequences were found to be identical to their corresponding cDNA infectious clones (data not shown).

Growth characteristics of 138.8v, 319.1v and 312.1v relative to BICv and CSICv were compared in a multistep growth curve by infecting primary swine macrophage cell cultures (MOI=0.1) and determining titers at various times post-infection (FIG. 7A). While growth characteristics of BICv, 138.8v, 319.1v and 312.1v were similar, CSICv growth was reduced by approximately 1000-fold. Notably, the plaque size of 138.8v and 319.1v was reduced by approximately 50 to 60% relative to BICv and 312.1v. The plaque size of the CSICv was reduced by 90% relative to BICv (FIG. 7B).

Chimeric viruses 319.1v and 312.1v were evaluated for swine virulence relative to BICv, CSICv, and 138.8v. Parental viruses exhibited characteristic virulence phenotypes (Table 6). Animals infected with chimeras 138.8v or 319.1v survived infection and, with the exception of a transient fever (1-2 days), remained clinically normal. All animals infected with 312.1v presented with clinical signs of CSFV starting at 3 to 7 DPI, with kinetics and severity of disease indistinguishable from those observed for animals infected with BICv (Table 6). White blood cell and platelet numbers dropped drastically in pBICv- and 312.1v-infected animals by 6 DPI, and remained low until death, while a transient and much less dramatic effect was observed for 312.1v- and 319.1v-infected animals (FIGS. 8A and 8B). CSICv infection induced no significant hematological changes.

Viremia in 138.8v- and 319.1v-infected animals was transient (8-10 DPI) and significantly reduced by $10^5$ to $10^6$ log$_{10}$ relative to BICv or 312.1v infection but was higher than that observed for CSICv-infected animals where no viremia was detected (FIG. 9C). Similar titration patterns were obtained for nasal swab and tonsil scraping samples (FIGS. 9A and 9B).

TABLE 6

Swine survival, clinical scores and fever response following infection with BICv, CSICv or chimeric viruses.

| Virus: | BICv | CSICv | 138.8v | 319.1v | 312.1v |
|---|---|---|---|---|---|
| # Survivors/Total | 0/6 | 4/4 | 6/6 | 6/6 | 0/6 |
| Mean time to death-Days | 12.2 (3.1) | — | — | — | 10.6 (2.1) |
| Clinical Scores Range | 11-20 | 1-1 | 1-1 | 1-1.5 | 10-20 |
| Fever: Days to Onset | 7 (0) | — | 9.5 (1.1) | 9.3 (1.2) | 5.0 (0.0) |
| Fever: Duration, # of Days | 5.2 (0.5) | — | 1 (0.5) | 1.25 (1.7) | 8 (0.7) |
| Fever: Max Temp. ° F. | 106.5 | 103.4 | 103.4 | 103.7 | 106.8 |

Nucleotide sequences of viruses recovered from infected animal tonsil-scraping samples (6DPI) were identical to 138.8v, 319.1v, and 312.1v stock viruses used for inoculation (data not shown).

For a more detailed comparison of the pathogenesis induced by the 138.8v, 319.1v, and 312.1 v, randomly selected animals were euthanized at 6 and 8 DPI (one animal/time point/group), and tissue samples (tonsil, submandibular lymph node, and spleen) were collected for virus titration, histopathological, and immunohistochemical analysis.

Virus tissue titers are shown in Table 7. Replication of CSICv, 138.8v, and 319.1v was transient in tonsils, with tissue titers significantly reduced (approximately 10 to $10^6$ $log_{10}$, depending on virus and time PI) relative to BICv and 312.1v. CSICv and 138.8v were not detected in regional draining submandibular lymph node or spleen tissues, and 319.1v was detected in these tissues only transiently (6 DPI) and at significantly reduced titers ($10^2$ $log_{10}$) relative to those observed for BICv and 312.1v.

TABLE 7

Virus titers in tissues following infection with BICv, CSICv or chimeric viruses.

| | | $Log_{10}/TCID_{50}/g$ | | |
|---|---|---|---|---|
| Virus | DPI | Tonsils | Mandibular Lymph Node | Spleen |
| BICv | 6 | 4.97 | 5.13 | 5.97 |
| | 8 | 5.47 | 5.97 | 5.80 |
| CSICv | 6 | Neg[a] | Neg | Neg |
| | 8 | 2.13 | Neg | Neg |
| 319.1v | 6 | 3.63 | 3.47 | 3.63 |
| | 8 | 3.13 | Neg | Neg |
| 138.8v | 6 | 2.80 | Neg | Neg |
| | 8 | Neg | Neg | Neg |
| 312.1v | 6 | 5.80 | 5.97 | 5.97 |
| | 8 | 6.30 | 7.30 | 7.13 |

[a]less than 1.8 $TCID_{50}$ ($log_{10}$)

Histological lesions in pigs inoculated with BICv were already present at 6 DPI (FIG. 10). This included tonsillar, splenic, and submandibular lymphoid necrosis and cell depletion along with a moderate to marked (6 and 8 DPI, respectively) histiocytic hyperplasia and reticuloendothelial cell proliferation. Additionally, the spleen was characterized by moderate to severe lymphoid follicular depletion, necrosis and a mild to moderate histiocytosis. Animals infected with viruses CSICv and 319.1v showed histopathological changes in tonsils and the regional submandibular lymph node similar to those described for the BICv-infected pigs, but the degree of severity was markedly reduced: there was minimal to mild lymphoid necrosis and depletion and a mild histiocytosis. Notably, the pathology already started to resolve, with evidence of lymphoid hyperplasia, at 6 DPI. In addition, spleens of animals infected with CSICv or 319.1v showed near negligible changes with minimal lympholysis and depletion (FIG. 10).

The presence of CSFV antigen in tissues of infected animals was consistent with the degree and distribution of lesions and virus tissue titers. In BICv-infected pigs there was antigen in superficial and cryptic tonsillar epithelial cells and tonsillar endothelium by 26 DPI. At 6 and 8 DPI, antigen was observed in tonsillar macrophages and lymphoid follicular and parafollicular dendritic cells with moderate to marked immunoreactivity (FIG. 10). Similar immunoreactivity was observed in the spleen where macrophages and endothelium were affected. Conversely, animals infected with CSICv or 319.1v showed CSFV antigen concentrated in the tonsil, with a significant relative reduction in immunoreactivity in the regional submandibular lymph node and spleen compared to the BICv-infected animals.

These data indicate that glycoprotein E2 markedly affects pig virulence. 319.1v infection is characterized by mild and transient clinical disease, decreased viral replication in tonsils, limited generalization of infection, and a significant reduction in virus shedding.

Example 9

Brescia Structural Protein E2 not Sufficient to Restore CS Virus Virulence

To test the ability of Brescia virus E2 to restore a virulent phenotype to the attenuated CS vaccine strain, two chimeric viruses which contained the genomic region encoding all Brescia virus structural proteins (343.8v) or the Brescia E2/p7/and the amino terminal 894 amino acid residues of NS2-3 proteins (137.1v) inserted into the CS genetic background were constructed and evaluated for virulence in swine (FIG. 3, Table 5). Both chimeric viruses demonstrated an attenuated phenotype, indicating that these Brescia genomic regions alone are not sufficient to restore a virulence phenotype to CS virus.

Example 10

Immunization, Challenge, and Clinical Analysis

Feeder pigs (4 to 6 weeks old, weaned at 3 weeks) were acclimated for approximately one week before entering vaccine trials. Experimental groups of 8 pigs each were intranasally inoculated with 105 $TCID_{50}$/ml of RB-C22v. Two control groups of 4 animals each were left without inoculation. At challenge (7 and 21 days post-inoculation), pigs were exposed to $10^5$ $TCID_{50}$/ml of pBIC by intranasal instillation (~1 ml of complete tissue culture supernatant). Studies were terminated on day 28 after challenge inoculation, by performing a necropsy of all animals. During the course of the study all animals were monitored twice a day as in Example 7. Animals with marked symptoms of disease and poor prognosis were sacrificed and subject to post-mortem exam. Nasal swabs, tonsil scrapings, and peripheral blood were obtained, as described in Example 7, from all pigs throughout the period of observation.

After the infection, none of the RB-C22v-infected pigs developed any CSF-related clinical signs, corroborating the complete attenuation of the RB-C22v. In contrast with results obtained with uninfected control animals, where mortality was 100%, all RB-C22v pre-infected animals survived the pBICv challenge and remained clinically normal, whether the challenge was conducted at 7 or 21 days post infection (DPI). On the other hand, all control, non-RB-C22v pre-infected animals presented clinical signs of CSFV between 3 to 7 days after the challenge, and these symptoms progressed until death in all the cases (Table 8).

TABLE 8

Swine survival, viremia and fever response in RB-C22 pre-infected animals challenged with CSFV Brescia.

| Day challenged post RB-C22v infection | Pre-infection with RB-C22v | Survivors/Total | Mean time to death | Mean time of fever onset Days | Mean time of fever duration (±SD) |
|---|---|---|---|---|---|
| 7 | Yes | 8/8 | No | No | No |
|   | No | 0/4 | 8.5 (1.72) | 5.25 (0.50) | 3.75 (1.89) |
| 21 | Yes | 8/8 | No | No | No |
|   | No | 0/4 | 9.75 (4.27) | 3.75 (0.50) | 4.5 (3.00) |

The temperature profile in animals challenged either at 7 or 21 days post RB-C22v inoculation demonstrated that they remained apyretic along the observational period (19 to 21 days). On the contrary, at 4-5 days post challenge (DPC) unvaccinated controls presented febrile temperatures (over 104° F.) which lasted until days 9-10 post challenge, when control animals started to die (between 6 to 14 DPC) (FIGS. 11A and 11B).

In conformance with the clinical symptoms and temperature profiles, blood cell counts (total white blood cells, lymphocytes, and platelets) dropped drastically in the RB-C22 uninfected challenged pigs and remained low until the time of death. In contrast, in the RB-C22v pre-infected animals, those parameters remained unchanged after the challenge throughout the experimental period and in fact increased in the group challenged at 7 days post RB-C22 infection (FIGS. 12A-12C).

When RB-C22v-infected animals, challenged 7 or 21 days after vaccination with CSFV strain Brescia, were tested 5 to 20 DPC, oronasal shedding of virus was reduced to levels below detection limits in both groups (Table 9). In contrast, significant amounts of virus, reaching up to $10^{5.8}$ $TCID_{50}$/ml, were present in nasal swabs from non-RB-C22v-infected control pigs. In accordance with these data, the presence of the challenge virus was consistently absent in tonsil scrapes from all RB-C22v-infected animals regardless of whether they were challenged at 7 days or 21 days after RB-C22v infection, while control animals showed significant virus titers (up to $10^{5.9}$ $TCID_{50}$/ml) (Table 9). To confirm the results obtained in nasal swabs and tonsil scrapings by virus titration, all negative samples were further analyzed by real time-RT-PCR and all samples were found to be negative. Finally, in blood samples taken at 7-9 DPC from animals in groups challenged either at 7 or 21 days post-RB-C22v infection, no virus could be detected by virus isolation (data not shown).

TABLE 9

Presence of virus in clinical samples from RB-C22 pre-infected animals challenged with CSFV Brescia.[a]

| | Tonsil Scraping | | | | Nasal Swabs | | | |
|---|---|---|---|---|---|---|---|---|
| | RB-C22 infected | | Control | | RB-C22 infected | | Control | |
| Days post challenge | $TCID_{50}$/ml | PCR | $TCID_{50}$/ml | PCR | $TCID_{50}$/ml | PCR | $TCID_{50}$/ml | PCR |
| (A) Animals challenged with Brescia virus 7 days after infection with RB-C22 | | | | | | | | |
| 5 | ≤1.80[b] | Neg. | 2.39 (1.60) | Pos. | ≤1.80 | Neg. | 3.14 (0.23) | Pos. |
| 7 | ≤1.80 | Neg. | 5.39 (0.83) | Pos. | ≤1.80 | Neg. | 4.80 (0.00) | Pos. |
| 9 | ≤1.80 | Neg. | D[c] | D | ≤1.80 | Neg. | 5.97 (0.00) | Pos. |
| 12 | ≤1.80 | Neg. | D | D | ≤1.80 | Neg. | D | D |
| 16 | ≤1.80 | Neg. | D | D | ≤1.80 | Neg. | D | D |
| 20 | ≤1.80 | Neg. | D | D | ≤1.80 | Neg. | D | D |
| (B) Animals challenged with Brescia virus 21 days after infection with RB-C22 | | | | | | | | |
| 5 | ≤1.80 | Neg. | 1.48 (1.72) | Pos. | ≤1.80 | Neg. | ≤1.80 | Pos. |
| 7 | ≤1.80 | Neg. | 3.96 (1.18) | Pos. | ≤1.80 | Neg. | 3.63 (0.00) | Pos. |
| 9 | ≤1.80 | Neg. | 5.30 (0.00) | Pos. | ≤1.80 | Neg. | 5.63 (0.00) | Pos. |
| 12 | ≤1.80 | Neg. | 3.80 (0.00) | Pos. | ≤1.80 | Neg. | 5.80 (0.00) | Pos. |
| 16 | ≤1.80 | Neg. | D | D | ≤1.80 | Neg. | D | D |
| 20 | ≤1.80 | Neg. | D | D | ≤1.80 | Neg. | D | D |

[a]Results are presented as virus titer, expressed as $TCID_{50}$/ml (±SD) and RT-PCR, expressed as positive or negative.
[b]Virus titers of ≤1.80 are undetectable
[c]D: dead animal

Example 11

Seroneutralization and ELISA Assays

The humoral immune response of pigs infected with RB-C22v was studied by measuring virus neutralizing activity as well as detecting E2-specific binding antibodies in ELISA. CSFV neutralization titers were determined as follows: Serial two-fold dilutions of each serum sample in MEM-5% FCS were mixed with an equal volume of a virus inoculum containing $TCID_{50}$ of CSFV strain Brescia in 96 well clusters (Becton Dickinson, Palo Alto, Calif.). After 1 h incubation at 37° C. in a moisturized chamber, approximately $10^3$ SK6 cells were added per well. Plates were incubated at 37° C. and 5% $CO_2$ for 4 days. Neutralization titers were recorded as the minimal concentration of monoclonal antibody capable to protect SK6 cell monolayers from CSFV infection detected by immunoperoxidase staining (see Example 1). Detection of CSFV-specific antibodies was detected using two commercially available kits: CSFV Antibody Test Kit (IDDex, Sweden) and CheKit CSF-Marker ELISA Test Kit (Bommeli, Switzerland) according to manufacturer's instructions. Results obtained from the two commercial kits were comparable.

Neutralizing antibodies were detected in 7 of 8 individuals as early as 14 days after RB-C22v infection; significant levels were detected in all animals (FIGS. 13A and 13B). Anti-E2 titers drastically increased in all RB-C22v-infected animals by day 5 after challenge with the Brescia virus (FIGS. 13A and 13B). No CSFV-specific antibodies were detected in control animals either by ELISA tests (both) or the neutralization assay.

Example 12

Detection of Early Protection Against Challenge in RB-C22v-Infected and 138.8v-Infected Animals Although RB-C22v-infected animals were completely protected by 7 days post RB-C22v infection, anti-CSFV antibody was not detected by ELISA or in the neutralization assay (FIGS. 13A and 13B). The presence of such protection in animals challenged after 7 days post-RB-C22v infection in the absence of CSFV-specific antibodies indicated that protection should be mediated by an antibody independent mechanism. In order to establish how early this mechanism was elicited in RB-C22v-infected animals, pigs were intranasally challenged with $10^5$ $TCID_{50}$ of Brescia virus at 1, 3, and 5 days after the infection with RB-C22v. All three animals challenged at 1 day after RB-C22v infection presented fever and CSFV symptoms beginning at the fifth day post-challenge (PC). Two of the three animals remained in this condition until the time of death (9 and 13 DPC, respectively), while the remaining animal was pyretic until day 12 PC, then the temperature returned to normal until the end of the observational period on day 16 PC. In accordance with the described symptoms, count values for total white cells, lymphocytes and platelets dropped drastically in all animals beginning day 3 PC (FIGS. 14A-14C). In contrast, animals challenged at 3 days post-RB-C22v infection develop a very transient fever (i.e., only one animal exhibited a fever over 104.5° F. by day 4 PC), without clinical symptoms, a transitory depression in white cells, lymphocyte and platelet counts (between 1 to 5 days PC) and 100% survival by day 15, at the end of the experimental period. Finally, all animals challenged at 5 days post RB-C22v infection also showed a transient fever, e.g., two animals exhibited a fever over 104.5° F. by day 3 PC, without a significant alteration of their blood cell parameters. No clinical symptoms were present during the experimental period (Table 10, FIGS. 14A-14C).

TABLE 10

Swine survival, viremia and fever response in RB-C22v pre-infected animals challenged 1, 3, and 5 days later with CSFV Brescia virus.

| Day challenged post RB-C22v infection | Survivors/Total | Mean time to death (±SD) | Mean time of fever onset (±SD) | Mean time of fever duration (±SD) |
|---|---|---|---|---|
| 1 | 1/3 | 12.66 (3.51) | 4 (0.00) | 7 (4.36) |
| 3 | 3/3 | No | 4 (2.31) | 1 (0.58) |
| 5 | 3/3 | No | 3 (1.73) | 1 (0.58) |

When 138.8v-infected animals were challenged with BICv, none of the six animals challenged at either 3 days or 28 days after 138.8v infection developed fever or showed CSFV symptoms. Animals that were not pre-infected developed clinical signs of CSF and fever (Table 11).

TABLE 11

Swine survival, viremia and fever response in 138.8v pre-infected animals challenged 3 and 28 days later with CSFV Brescia virus.

| Infecting Virus | Challenge Virus | Time of Challenge (days post-infection) | Survivors/ Total | CSF Clinical Signs | Mean Time Fever Onset Days (SD) |
|---|---|---|---|---|---|
| 138.8v | BICv | 3 | 6/6 | No | No |
| 138.8v | BICv | 28 | 6/6 | No | No |
| None | BICv | — | 0/6 | Yes | 6.18 (0.42) |

In order to determine the mechanism of interference between RB-C22v and Brescia which could mediate protection at early stages after RB-C22v infection, we assayed for presence of virus, within the first 72 h after challenge, in those lymphatic organs where the virus replicates after the intranasal challenge. Tonsils are the first place where CSFV replicated during infection by the oronasal route. After the intranasal infection with Brescia, infectious virus could not be detected in tonsil tissues from control animals until 48 h after infection. However, by real time RT-PCR, virus RNA was detected as early as 6 h post infection (Table 12). In animals challenged at 24 h after RB-C22v infection, virus titers were not detected until 24 h PC. By real time PCR, RNA virus is detected at 6 h (in one out of two tested animals) and in the two analyzed animals at 24 h post challenge (Table 12).

TABLE 12

| Animals challenged with Brescia virus 1 and 3 days post RB-C22v infection.[a] | | | | | | |
|---|---|---|---|---|---|---|
| Hours | Tonsils | | | Mandibular Lymph Node | | |
| PC | 1 DPI | 3 DPI | Control[c] | 1 DPI | 3 DPI | Control |
| 6 | ≦1.80[b] (±) | 2.47 (0.71)(+/+) | ≦1.80 (+) | ≦1.80 (±) | 3.55 (0.11)(+/+) | ≦1.80 (−) |
| 12 | ≦1.80 (±) | 4.21 (0.92)(+/+) | ≦1.80 (+) | ≦1.80 (±) | 4.05 (0.49)(+/+) | ≦1.80 (−) |
| 24 | 1.97 (0.00)(+/+) | 6.39 (0.59)(+/+) | ≦1.80 (+) | ≦1.80 (±) | 4.47 (1.20)(+/+) | ≦1.80 (−) |
| 48 | 2.05 (0.11)(+/+) | 4.80 (0.49)(+/+) | 2.83 (0.00)(+) | 3.30 (0.95)(+/+) | 4.22 (1.20)(+/+) | 1.97 (0.00)(+) |
| 72 | 5.72 (1.20)(+/+) | 4.80 (1.65)(+/+) | 5.68 (0.00)(+) | 4.22 (0.12)(+/+) | 2.80 (0.95)(+/+) | 4.63 (0.00)(+) |
| Hours | Blood | | | Spleen | | |
| PC | 1 DPI | 3 DPI | Control | 1 DPI | 3 DPI | Control |
| 6 | ≦1.80 | ≦1.80 | ≦1.80 | ≦1.80(−/−) | ≦1.80(+/+) | ≦1.80(−) |
| 12 | ≦1.80 | ≦1.80 | ≦1.80 | ≦1.80(−/−) | 2.13(+/+) | ≦1.80(−) |
| 24 | ≦1.80 | 2.95 (0.82) | ≦1.80 | ≦1.80(+/+) | 2.97(0) (+/+) | ≦1.80(+) |
| 48 | ≦1.80 | 2.13 (0.50) | ≦1.80 | ≦1.80(+/+) | 2.22 (0.12)(+/+) | ≦1.80(+) |
| 72 | ≦1.80 | ≦1.80 | 2.13 (0.00) | 4.22 (2.44(+/+) | 2.80 (0.94)(+/+) | 3.30 (0.00)(+) |

[a]Results are presented as virus titer, expressed as $TCID_{50}$/ml (±SD) and rt-RT-PCR, expressed as positive (+) or negative (−).
[b]Virus titers of ≦1.80: undetectable
[c]Control: animals that were not pre-infected with RB-C22v Using a virus-specific conventional PCR (which is 20 times less sensitive than real time RT-PCR-data not shown), it was possible to show that beginning at 48 h PC, both viruses (RB-C22 and Brescia) were present in approximately equivalent amounts (Table 13). On the other hand, analysis of the tonsils from animals challenged with Brescia at 3 days after RB-C22 infection demonstrated that infectious virus is detected in all samples, showing an increase of $10^2$ to $10^4$ $\log_{10}$ in titers from the first to the last sample take, i.e., at 6 and 72 h post challenge, respectively. In all cases, the RNA isolated exclusively belongs to the RB-C22v (Table 13).

The mandibular lymph nodes are the draining regional lymphoid nodes for the tonsils. Thus, it was analyzed could be detected earlier than 48 h PC (Table 12). In animals infected with RB-C22v and challenged at 24 h with Brescia, infectious virus was detected at 48 h PC. At 6 h PC, one out of two animals sampled was positive by real time RT-PCR; however, thereafter, all samples were positive. The analysis of the type of virus present in the samples, by RT-PCR, demonstrated that a mixture of RB-C22 and Brescia viruses were detected at 48 and 72 hr PC (Table 13). The analysis of the mandibular lymph nodes from animals challenged with Brescia at 72 h after RB-C22v infection demonstrated that infectious virus are detected in all samples and that the isolated RNA is exclusively RB-C22v (Table 13).

TABLE 13

| Detection of the type of virus (RB-C22v or Brescia) isolated from animals challenged with Brescia virus 1 and 5 days post RB-C22v infection. | | | | | | | | | |
|---|---|---|---|---|---|---|---|---|---|
| Hour | Tonsils | | | Mandibular Lymph Node | | | Spleen | | |
| PC | 1 DPI | 3 DPI | Control | 1 DPI | 3 DPI | Control | 1 DPI | 3 DPI | Control |
| 6 | Neg/Neg* | Neg/C22 | Neg | Neg/Neg | C22/C22 | Neg | Neg/Neg | Neg/Neg | Neg |
| 12 | Neg/Neg | C22/C22 | Neg | Neg/Neg | C22/C22 | Neg | Neg/Neg | Neg/Neg | Neg |
| 24 | Neg/Neg | C22/C22 | Neg | Neg/Neg | C22/C22 | Neg | Neg/Neg | C22/C22 | Neg |
| 48 | Neg/ C22-Brescia | C22/C22 | Brescia | C22/Brescia/ C22/Brescia | C22/C22 | Brescia | Neg/Neg | C22/C22 | Brescia |
| 72 | C22/Brescia/ C22/Brescia | C22/C22 | Brescia | C22/Brescia/ C22/Brescia | C22/C22 | Brescia | C22/Brescia/ C22/Brescia | C22/C22 | Brescia |

*Two animals were used in each time point.

whether the interactions between RB-C22 and Brescia viruses in tonsils would influence the spreading of a determined virus to the rest of the target organs. In animals infected with Brescia, neither infectious virus nor viral RNA As a marker for the generalization of the infection, the presence and type of virus present in the spleen of the RB-C22v-infected and challenged animals was determined. Infectious Brescia virus was not detected in control animals earlier than 72 h PC; however, by real time RT-PCR, viral RNA was detected beginning at 48 h post-infection. The spleens of animals challenged at 24 h PI with RB-C22v showed the presence of infectious virus starting at 48 h PC; while viral RNA was detected, by real time RT-PCR, as early as at 24 h PC. The identification of the acting virus, detected at 72 h PC by specific RT-PCR, indicated that both viruses (RB-C22 and Brescia) were present in approximately equivalent amounts. The analysis of the spleen from animals challenged with Brescia at 72 h after RB-C22v infection showed that infectious virus are detected in all the samples beginning at 12 h PC. By real time RT-PCR, viral RNA could be detected beginning at 6 h PC. In all samples, beginning at 24 h PC, the isolated RNA belongs to the RB-C22v (Table 13).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant classical swine fever virus comprising DNA which has been modified to encode a CSFV E1 glycoprotein comprising a 19 mer peptide insertion.

2. The recombinant CSF virus according to claim 1 wherein DNA encoding said 19 mer peptide insertion comprises SEQ ID NO:27.

3. A recombinant classical swine fever virus comprising DNA encoding CSFV E2 glycoprotein which has been modified by replacing the E2 gene of the highly pathogenic strain Brescia which the E2 gene from vaccine strain CS, a modification resulting in attenuation of CSFV.

4. An isolated nucleic acid encoding an antigenic CSFV E1 glycoprotein wherein said glycoprotein comprises a 19 mer peptide insertion.

5. The isolated nucleic acid of claim 4 wherein said nucleic acid encoding the 19 mer peptide insertion has the sequence set forth in SEQ ID NO:27.

6. The isolated nucleic acid of claim 4 wherein said nucleic acid encoding the antigenic CSFV E1 glycoprotein has the sequence set forth in SEQ ID NO:29.

7. An isolated polypeptide having the sequence set forth in SEQ ID NO:28.

8. An isolated antigenic CSFV E1 glycoprotein having the sequence set forth in SEQ ID NO:30.

9. A rationally designed live attenuated CSF vaccine comprising a recombinant classical swine fever virus according to any one of claims 1, 2, and 3.

10. An immunogenic composition comprising a viable recombinant classical swine fever virus comprising DNA encoding CSFV E2 glycoprotein which has been modified by replacing the E2 gene of the highly pathogenic strain Brescia with the E2 gene from vaccine strain CS, a modification resulting in attenuation of CSFV.

11. An immunogenic composition comprising a viable recombinant classical swine fever virus comprising DNA modified to encode a CSFV E1 glycoprotein comprising a 19 mer peptide insertion.

12. A method of producing a recombinant classical swine fever virus comprising DNA modified to encode a CSFV E1 glycoprotein comprising a 19 mer peptide insertion.

13. A method of producing a recombinant classical swine fever virus comprising DNA encoding CSFV E2 glycoprotein which has modified by replacing the E2 gene of the highly pathogenic strain Brescia with the E2 gene from vaccine strain CS, a modification resulting in attenuation of CSFV.

14. A kit for generating an immune response against classical swine fever virus comprising an immunogenic composition comprising a viable recombinant classical swine fever virus according to any one of claims 10 and 11.

* * * * *

SEQUENCE LISTING

```
<160> NUMBER OF SEQ ID NOS: 33

<210> SEQ ID NO 1
<211> LENGTH: 54
<212> TYPE: DNA
<213> ORGANISM: Classical Swine Fever Virus

<400> SEQUENCE: 1
acgtcactag tcacgcgtat atgcatatgg ccgtagcggc catccatggc tcga           54

<210> SEQ ID NO 2
<211> LENGTH: 45
<212> TYPE: DNA
<213> ORGANISM: Classical Swine Fever Virus

<400> SEQUENCE: 2
cactagtcac gcgtatatgc atatggccta gcggccatcc atggc                    45

<210> SEQ ID NO 3
<211> LENGTH: 18
<212> TYPE: DNA
<213> ORGANISM: Classical Swine Fever Virus

<400> SEQUENCE: 3
ctcctgctat ttcatcta                                                  18

<210> SEQ ID NO 4
<211> LENGTH: 47
<212> TYPE: DNA
<213> ORGANISM: Classical Swine Fever Virus

<400> SEQUENCE: 4
actagtacgc gttaatacga ctcactatag tatacgaggt tagttca                  47

<210> SEQ ID NO 5
<211> LENGTH: 46
<212> TYPE: DNA
<213> ORGANISM: Classical Swine Fever Virus

<400> SEQUENCE: 5
gtcagtcgac ttaatacgac tcactatagt atacgaggtt agttca                   46

<210> SEQ ID NO 6
<211> LENGTH: 18
<212> TYPE: DNA
<213> ORGANISM: Classical Swine Fever Virus
```

```
<400> SEQUENCE: 6
gcgagttgtt ctgttaga                                                  18

<210> SEQ ID NO 7
<211> LENGTH: 18
<212> TYPE: DNA
<213> ORGANISM: Classical Swine Fever Virus

<400> SEQUENCE: 7
atccatttct ttataggc                                                  18

<210> SEQ ID NO 8
<211> LENGTH: 18
<212> TYPE: DNA
<213> ORGANISM: Classical Swine Fever Virus

<400> SEQUENCE: 8
ccctatccta tcatccgt                                                  18

<210> SEQ ID NO 9
<211> LENGTH: 18
<212> TYPE: DNA
<213> ORGANISM: Classical Swine Fever Virus

<400> SEQUENCE: 9
gtgttctctt ctgctcac                                                  18

<210> SEQ ID NO 10
<211> LENGTH: 18
<212> TYPE: DNA
<213> ORGANISM: Classical Swine Fever Virus

<400> SEQUENCE: 10 gggggggcaat tggacatg                                                 18

<210> SEQ ID NO 11
<211> LENGTH: 21
<212> TYPE: DNA
<213> ORGANISM: Classical Swine Fever Virus

<400> SEQUENCE: 11
gggccgttag aaattacctt a                                              21

<210> SEQ ID NO 12
<211> LENGTH: 34
<212> TYPE: DNA
<213> ORGANISM: Classical Swine Fever Virus

<400> SEQUENCE: 12
attgccatgg cccgggccgt tagaaattac ctta                                34

<210> SEQ ID NO 13
<211> LENGTH: 18
<212> TYPE: DNA
<213> ORGANISM: Classical Swine Fever Virus

<400> SEQUENCE: 13
aagcgatggt ttgctagg                                                  18

<210> SEQ ID NO 14
<211> LENGTH: 20
<212> TYPE: DNA
<213> ORGANISM: Classical Swine Fever Virus
```

-continued

<400> SEQUENCE: 14
cctcatctgc ttgataaaag                                                   20

<210> SEQ ID NO 15
<211> LENGTH: 18
<212> TYPE: DNA
<213> ORGANISM: Classical Swine Fever Virus

<400> SEQUENCE: 15
ccttctctgg gcttgttc                                                     18

<210> SEQ ID NO 16
<211> LENGTH: 29
<212> TYPE: DNA
<213> ORGANISM: Classical Swine Fever Virus

<400> SEQUENCE: 16
gaacaactcg ccgcgggtct acagttagg                                         29

<210> SEQ ID NO 17
<211> LENGTH: 29
<212> TYPE: DNA
<213> ORGANISM: Classical Swine Fever Virus

<400> SEQUENCE: 17
cctaactgta gacccgcggc gagttgttc                                         29

<210> SEQ ID NO 18
<211> LENGTH: 37
<212> TYPE: DNA
<213> ORGANISM: Classical Swine Fever Virus

<400> SEQUENCE: 18
ccggccgcgt cgacatagat ctatggccgt agcggcc                                37

<210> SEQ ID NO 19
<211> LENGTH: 45
<212> TYPE: DNA
<213> ORGANISM: Classical Swine Fever Virus

<400> SEQUENCE: 19
tcgaggccgc tacggccata gatctatgtc gacgcggccg gacgt                       45

<210> SEQ ID NO 20
<211> LENGTH: 18
<212> TYPE: DNA
<213> ORGANISM: Classical Swine Fever Virus

<400> SEQUENCE: 20
gattctccat gagatggg                                                     18

<210> SEQ ID NO 21
<211> LENGTH: 35
<212> TYPE: DNA
<213> ORGANISM: Classical Swine Fever Virus

<400> SEQUENCE: 21
attgctcgag cccgggccgt taggaaatta cctta                                  35

<210> SEQ ID NO 22
<211> LENGTH: 18
<212> TYPE: DNA

```
<213> ORGANISM: Classical Swine Fever Virus

<400> SEQUENCE: 22
gatgaattag tcaaggag                                                  18

<210> SEQ ID NO 23
<211> LENGTH: 18
<212> TYPE: DNA
<213> ORGANISM: Classical Swine Fever Virus

<400> SEQUENCE: 23
acacaactgt caaggtgc                                                  18

<210> SEQ ID NO 24
<211> LENGTH: 18
<212> TYPE: DNA
<213> ORGANISM: Classical Swine Fever Virus

<400> SEQUENCE: 24
tctgtaacct gtctcatt                                                  18

<210> SEQ ID NO 25
<211> LENGTH: 60
<212> TYPE: DNA
<213> ORGANISM: Classical Swine Fever Virus

<400> SEQUENCE: 25
tggctgttac tggtaactgg ggcacaaggc cggctagcct gcaaggaaga tcacaggtac    60

<210> SEQ ID NO 26
<211> LENGTH: 20
<212> TYPE: PRT
<213> ORGANISM: Classical Swine Fever Virus

<400> SEQUENCE: 26

Trp Leu Leu Leu Val Thr Gly Ala Gln Gly Arg Leu Ala Cys Lys Glu
 1               5                  10                  15

Asp His Arg Tyr
            20

<210> SEQ ID NO 27
<211> LENGTH: 57
<212> TYPE: DNA
<213> ORGANISM: Classical Swine Fever Virus

<400> SEQUENCE: 27
ggggcacctg tctcttgtac acatcttgcg gccgcaagat gtgtacaaga gcacgct       57

<210> SEQ ID NO 28
<211> LENGTH: 19
<212> TYPE: PRT
<213> ORGANISM: Classical Swine Fever Virus

<400> SEQUENCE: 28

Gly Ala Pro Val Ser Cys Thr His Leu Ala Ala Ala Arg Cys Val Gln
 1               5                  10                  15

Glu Thr Ala

<210> SEQ ID NO 29
<211> LENGTH: 117
<212> TYPE: DNA
<213> ORGANISM: Classical Swine Fever Virus
```

-continued

```
<400> SEQUENCE: 29
tggctgttac tggtaactgg ggcacctgtc tcttgtacac atcttgcggc cgcaagatgt         60
gtacaagaga cagctggggc acaaggccgg ctagcctgca aggaagatca caggtac          117

<210> SEQ ID NO 30
<211> LENGTH: 39
<212> TYPE: PRT
<213> ORGANISM: Classical Swine Fever Virus

<400> SEQUENCE: 30

Trp Leu Leu Leu Val Thr Gly Ala Pro Val Ser Cys Thr His Leu Ala
1               5                   10                  15

Ala Ala Arg Cys Val Gln Glu Thr Ala Gly Ala Gln Gly Arg Leu Ala
            20                  25                  30

Cys Lys Glu Asp His Arg Tyr
        35

<210> SEQ ID NO 31
<211> LENGTH: 18
<212> TYPE: DNA
<213> ORGANISM: Classical Swine Fever Virus

<400> SEQUENCE: 31
tctgtaacct gtctcatt                                                      18

<210> SEQ ID NO 32
<211> LENGTH: 17
<212> TYPE: DNA
<213> ORGANISM: Classical Swine Fever Virus

<400> SEQUENCE: 32
tcatcagtct ggaatgt                                                       17

<210> SEQ ID NO 33
<211> LENGTH: 18
<212> TYPE: DNA
<213> ORGANISM: Classical Swine Fever Virus

<400> SEQUENCE: 33
gtcatccccc atttcctc                                                      18
```